(12) United States Patent
Fleischman et al.

(10) Patent No.: US 6,494,889 B1
(45) Date of Patent: Dec. 17, 2002

(54) ADDITIONAL SUTURELESS ANASTOMOSIS EMBODIMENTS

(75) Inventors: Sidney D. Fleischman, Menlo Park, CA (US); Russell A. Houser, Livermore, CA (US); James G. Whayne, San Jose, CA (US)

(73) Assignee: Converge Medical, Inc., Sunnyvale, CA (US)

( * ) Notice: Subject to any disclaimer, the term of this patent is extended or adjusted under 35 U.S.C. 154(b) by 261 days.

(21) Appl. No.: 09/654,216

(22) Filed: Sep. 1, 2000

Related U.S. Application Data

(60) Provisional application No. 60/151,863, filed on Sep. 1, 1999.

(51) Int. Cl.$^7$ .............................................. A61B 17/08
(52) U.S. Cl. ....................................... 606/155; 606/153
(58) Field of Search ................................ 606/151, 152, 606/153, 155, 156, 157, 158

(56) References Cited

U.S. PATENT DOCUMENTS

| | | |
|---|---|---|
| 4,214,587 A | 7/1980 | Sakura, Jr. |
| 4,366,819 A | 1/1983 | Kaster |
| 4,368,736 A | 1/1983 | Kaster |
| 4,607,637 A | 8/1986 | Berggren et al. |
| 4,624,257 A | 11/1986 | Berggren et al. |
| 4,657,019 A | 4/1987 | Walsh et al. |
| 4,665,906 A | 5/1987 | Jervis |
| 4,787,386 A | 11/1988 | Walsh et al. |
| 4,917,087 A | 4/1990 | Walsh et al. |
| 4,917,090 A | 4/1990 | Berggren et al. |

(List continued on next page.)

FOREIGN PATENT DOCUMENTS

| | | |
|---|---|---|
| EP | 824 901 A2 A3 | 2/1998 |
| EP | 894 475 A1 | 2/1999 |
| WO | WO 96/22745 A1 | 8/1996 |
| WO | WO 97/13463 A1 | 4/1997 |
| WO | WO 97/13471 A1 | 4/1997 |
| WO | WO 97/16122 A1 | 5/1997 |
| WO | WO 97/27893 A1 | 8/1997 |
| WO | WO 97/27897 A1 | 8/1997 |
| WO | WO 97/27898 A1 | 8/1997 |
| WO | WO 97/31575 A1 | 9/1997 |

(List continued on next page.)

OTHER PUBLICATIONS

Yusuf, S. W. et al. (1994). "Transfemoral Endoluminal Repair of Abdominal Aortic Aneurysm with Bifuricated Graft," *Lancet* 344(8923):650–651.

Cragg et al. (1982). "Endovascular Diathermic Vessel Occlusion," *Radiology* 144:303–308.

Gorisch et al. (1982). "Heat–Induced Contraction of Blood Vessels," *Lasers in Surgery and Medicine* 2:1–13.

Heijmen, et al. (1999). "A novel one–shot anastomotic stapler prototype for coronary bypass grafting on the beating heart: Feasibility in the pig," *J. Thorac. Cardiovasc. Surg.* 117(1): 117–25.

*Primary Examiner*—David O. Reip
(74) *Attorney, Agent, or Firm*—Morrison & Foerster LLP

(57) ABSTRACT

This invention is related to devices and systems for creating sutureless anastomoses. In particular, this invention is related to devices for deploying and securing the ends of bypass grafts designed to provide a fluid flow passage between at least two vessels or tubular structures. A variety of compressible, expandable fittings, loading and delivery sheaths, tools, and other devices for creating end-end and end-side anastomoses, as well as methods for their use, are disclosed. In addition, robotic, remotely operable systems and devices for creating sutureless anastomoses in minimally invasive applications are disclosed. The systems of this invention do not require stopping or re-routing blood flow to perform an anastomosis between a bypass graft and a host vessel. Accordingly, this invention describes sutureless anastomosis systems that do not require cardiopulmonary bypass support when treating coronary artery disease.

7 Claims, 13 Drawing Sheets

U.S. PATENT DOCUMENTS

| | | |
|---|---|---|
| 4,917,091 A | 4/1990 | Berggren et al. |
| 4,950,227 A | 8/1990 | Savin et al. |
| 5,067,957 A | 11/1991 | Jervis |
| 5,078,736 A | 1/1992 | Behl |
| 5,156,613 A | 10/1992 | Sawyer |
| 5,190,546 A | 3/1993 | Jervis |
| 5,234,447 A | 8/1993 | Kaster et al. |
| 5,391,156 A | 2/1995 | Hildwein et al. |
| 5,405,322 A | 4/1995 | Lennox et al. |
| 5,443,497 A | 8/1995 | Venbrux |
| 5,503,635 A | 4/1996 | Sauer et al. |
| 5,571,167 A | 11/1996 | Maginot |
| 5,591,226 A | 1/1997 | Trerotola et al. |
| 5,597,378 A | 1/1997 | Jervis |
| 5,628,784 A | 5/1997 | Strecker |
| 5,657,429 A | 8/1997 | Wang et al. |
| 5,665,117 A | 9/1997 | Rhodes |
| 5,669,934 A | 9/1997 | Sawyer |
| 5,676,670 A | 10/1997 | Kim |
| 5,690,675 A | 11/1997 | Sawyer et al. |
| 5,695,504 A | 12/1997 | Gifford, III et al. |
| 5,697,968 A | 12/1997 | Rogers et al. |
| 5,702,418 A | 12/1997 | Ravenscroft |
| 5,713,917 A | 2/1998 | Leonhardt et al. |
| 5,720,755 A | 2/1998 | Dakov |
| 5,725,544 A | 3/1998 | Rygaard |
| 5,728,133 A | 3/1998 | Kontos |
| 5,749,375 A | 5/1998 | Maginot |
| 5,749,895 A | 5/1998 | Sawyer et al. |
| 5,755,775 A | 5/1998 | Trerotola et al. |
| 5,755,778 A | 5/1998 | Kleshinki |
| 5,762,458 A | 6/1998 | Wang et al. |
| 5,779,718 A | 7/1998 | Green et al. |
| 5,797,920 A | 8/1998 | Kim |
| 5,797,934 A | 8/1998 | Rygaard |
| 5,810,884 A | 9/1998 | Kim |
| 5,814,005 A | 9/1998 | Barra et al. |
| 5,824,015 A | 10/1998 | Sawyer |
| 5,861,003 A | 1/1999 | Latson et al. |
| 5,868,759 A | 2/1999 | Peyser et al. |
| 5,868,761 A | 2/1999 | Nicholas et al. |
| 5,868,770 A | 2/1999 | Rygaard |
| 5,871,536 A | 2/1999 | Lazarus |
| 5,931,842 A | 8/1999 | Goldsteen et al. |
| 5,934,286 A | 8/1999 | Maginot |
| 5,938,672 A | 8/1999 | Nash |
| 5,938,696 A | 8/1999 | Goicoechea et al. |
| 5,944,019 A | 8/1999 | Knudson et al. |
| 5,944,730 A | 8/1999 | Nobles et al. |
| 5,944,738 A | 8/1999 | Amplatz et al. |
| 5,944,750 A | 8/1999 | Tanner et al. |
| 5,954,735 A | 9/1999 | Rygaard |
| 5,957,940 A | 9/1999 | Tanner et al. |
| 5,964,782 A | 10/1999 | Lafontaine et al. |
| 5,968,053 A | 10/1999 | Revelas |
| 5,968,089 A | 10/1999 | Krajicek |
| 5,968,090 A | 10/1999 | Ratcliff et al. |
| 5,972,017 A | 10/1999 | Berg et al. |
| 5,972,023 A | 10/1999 | Tanner et al. |
| 5,976,178 A | 11/1999 | Goldsteen et al. |
| 5,979,455 A | 11/1999 | Maginot |
| 5,984,955 A | 11/1999 | Wisselink |
| 5,989,276 A | 11/1999 | Houser et al. |
| 5,989,287 A | 11/1999 | Yang et al. |
| 5,993,468 A | 11/1999 | Rygaard |
| 6,001,124 A | 12/1999 | Bachinski |
| 6,004,347 A | 12/1999 | McNamara et al. |
| 6,007,576 A | 12/1999 | McClellan |
| 6,010,529 A | 1/2000 | Herweck et al. |
| 6,017,352 A | 1/2000 | Nash et al. |
| 6,019,788 A | 2/2000 | Butters et al. |
| 6,030,370 A | 2/2000 | Kupka et al. |
| 6,030,392 A | 2/2000 | Dakov |
| 6,030,395 A | 2/2000 | Nash et al. |
| 6,036,702 A | 3/2000 | Bachinski et al. |
| 6,036,703 A | 3/2000 | Evans et al. |
| 6,036,705 A | 3/2000 | Nash et al. |
| 6,048,362 A | 4/2000 | Berg |
| 6,056,762 A | 5/2000 | Nash et al. |
| 6,059,824 A | 5/2000 | Taheri |
| 6,063,114 A | 5/2000 | Nash et al. |
| 6,068,654 A | 5/2000 | Berg et al. |
| 6,071,305 A | 6/2000 | Brown et al. |
| 6,074,416 A | 6/2000 | Berg et al. |
| 6,113,612 A | 9/2000 | Swanson et al. |
| 6,117,147 A | 9/2000 | Simpson et al. |
| 6,120,432 A | 9/2000 | Sullivan et al. |
| 6,149,681 A | 11/2000 | Houser et al. |
| 6,293,955 B1 | 9/2001 | Houser et al. |

FOREIGN PATENT DOCUMENTS

| | | |
|---|---|---|
| WO | WO 97/40754 A1 | 11/1997 |
| WO | WO 97/43961 A1 | 11/1997 |
| WO | WO 98/03118 A1 | 1/1998 |
| WO | WO 98/06356 A1 | 2/1998 |
| WO | WO 98/07399 A1 | 2/1998 |
| WO | WO 98/08456 A1 | 3/1998 |
| WO | WO 98/19608 A1 | 5/1998 |
| WO | WO 98/19618 A1 | 5/1998 |
| WO | WO 98/19629 A2 | 5/1998 |
| WO | WO 98/19630 A2 | 5/1998 |
| WO | WO 98/19631 A1 | 5/1998 |
| WO | WO 98/19632 A1 | 5/1998 |
| WO | WO 98/19634 A2 | 5/1998 |
| WO | WO 98/19635 A1 | 5/1998 |
| WO | WO 98/19636 A2 | 5/1998 |
| WO | WO 98/19732 A1 | 5/1998 |
| WO | WO 98/19625 A2 A3 | 5/1998 |
| WO | WO 98/38939 A1 | 9/1998 |
| WO | WO 98/38941 A1 | 9/1998 |
| WO | WO 98/40036 A1 | 9/1998 |
| WO | WO 98/42262 A1 | 10/1998 |
| WO | WO 98/52474 A1 | 11/1998 |
| WO | WO 98/55027 A2 | 12/1998 |
| WO | WO 98/57590 A1 | 12/1998 |
| WO | WO 98/57591 A1 | 12/1998 |
| WO | WO 98/57592 A1 | 12/1998 |
| WO | WO 99/00055 A2 | 1/1999 |
| WO | WO 99/18887 A1 | 4/1999 |
| WO | WO 99/38454 A2 | 8/1999 |
| WO | WO 99/45852 A2 | 9/1999 |
| WO | WO 99/48427 A1 | 9/1999 |
| WO | WO 99/62408 A1 | 12/1999 |
| WO | WO 99/62415 A1 | 12/1999 |
| WO | WO 99/63910 A1 | 12/1999 |
| WO | WO 99/65409 A1 | 12/1999 |
| WO | WO 00/09040 A1 | 2/2000 |
| WO | WO 00/15144 A1 | 3/2000 |
| WO | WO 00/24339 A1 | 5/2000 |
| WO | WO 00/27311 A1 | 5/2000 |
| WO | WO 00/27313 A2 A3 | 5/2000 |
| WO | WO 00/40176 A1 | 7/2000 |
| WO | WO 00/53104 A1 | 9/2000 |
| WO | WO 01/41653 A2 A3 | 6/2001 |

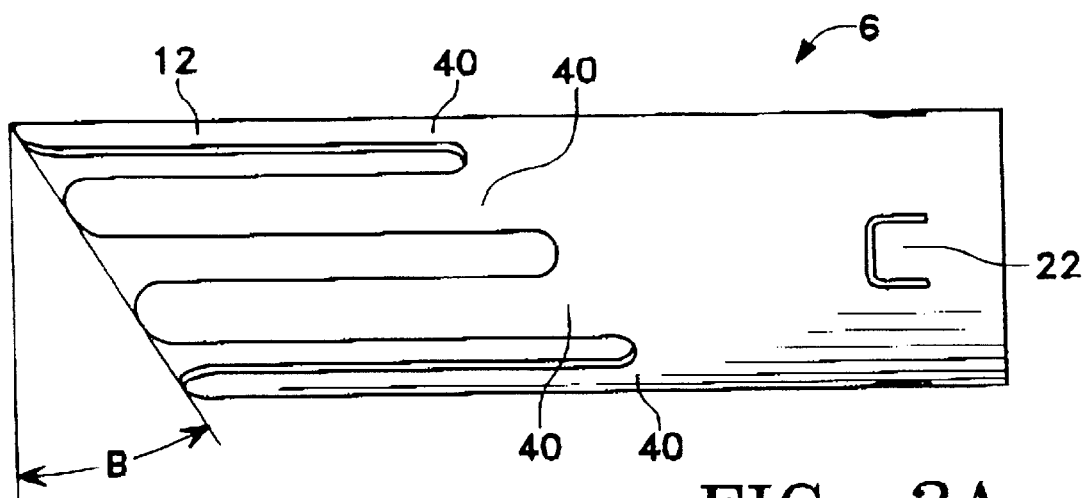
FIG. 3A
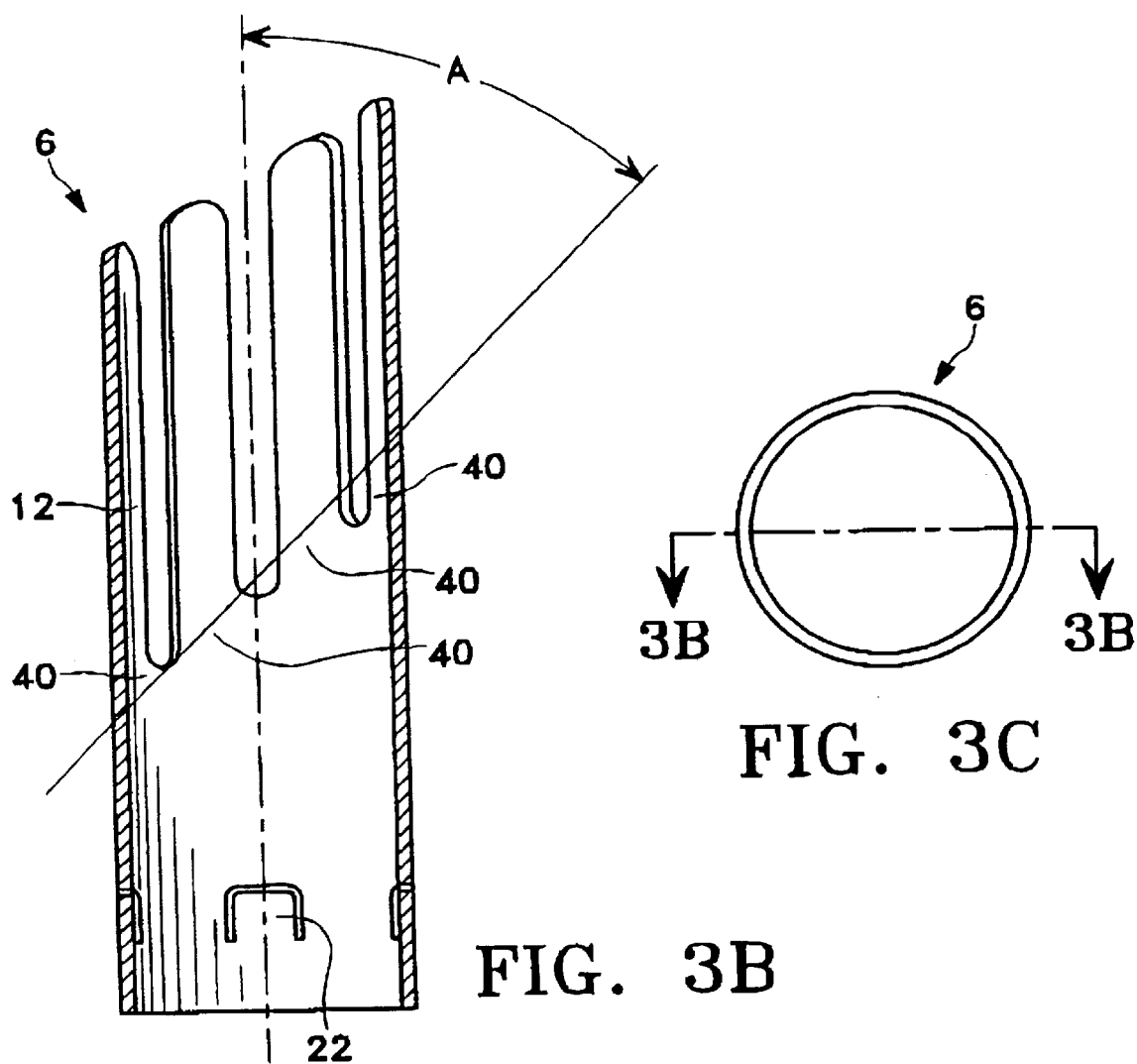
FIG. 3C
FIG. 3B

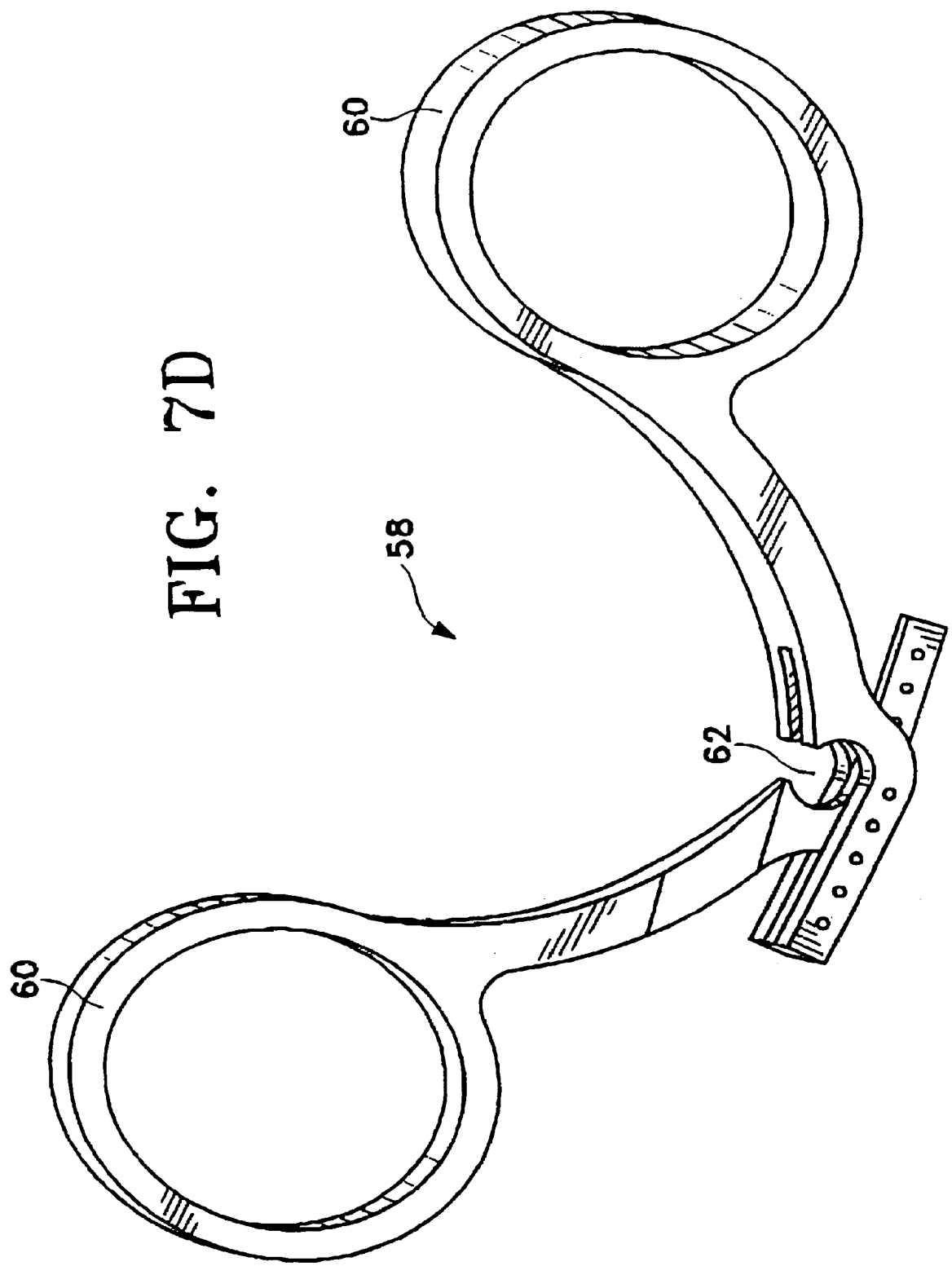

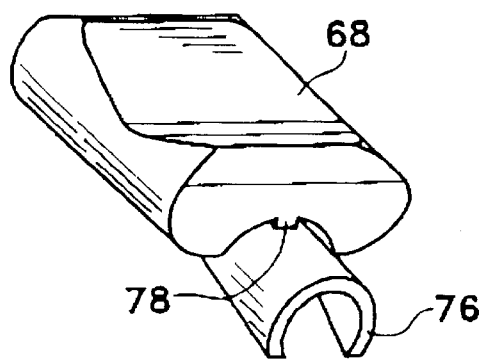
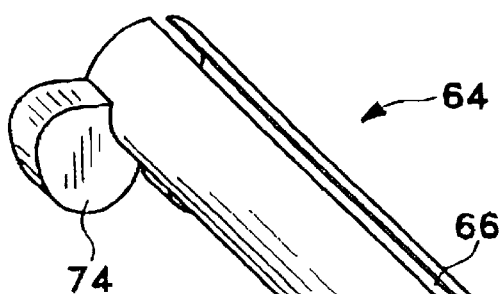
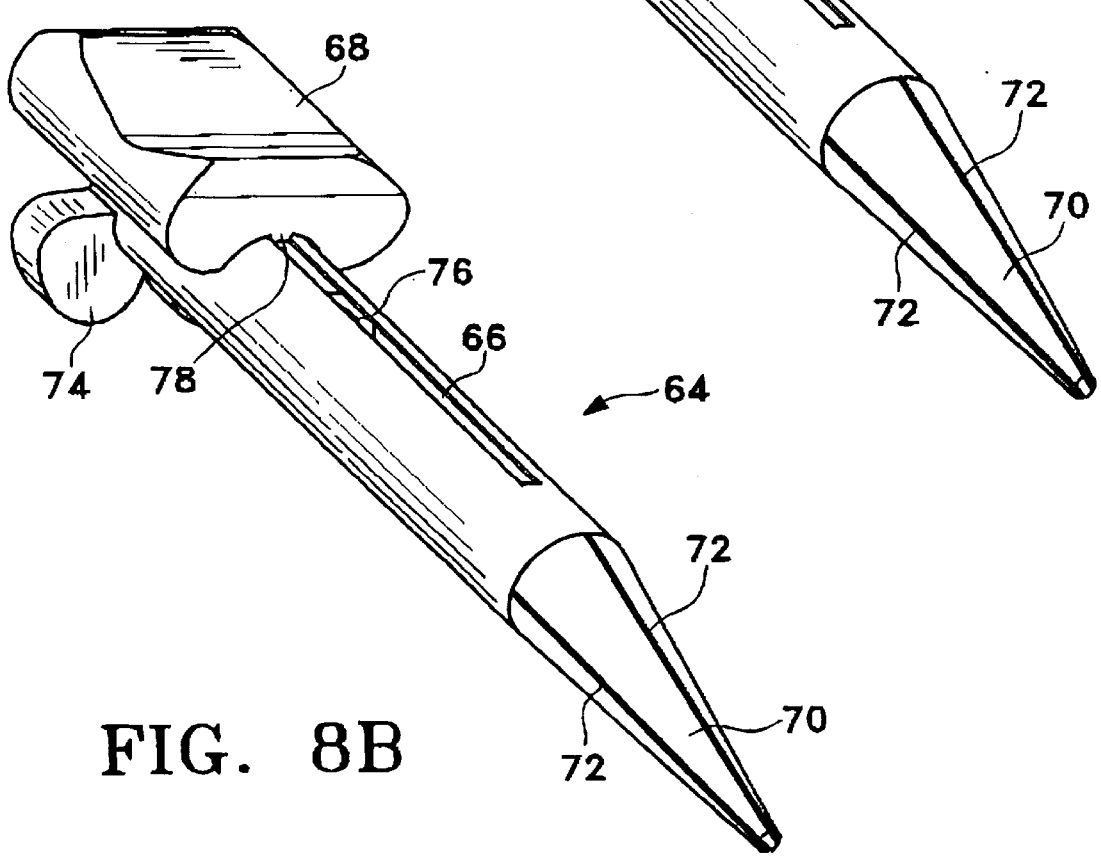
FIG. 8A
FIG. 8B

ADDITIONAL SUTURELESS ANASTOMOSIS EMBODIMENTS

CROSS-REFERENCE TO RELATED APPLICATIONS

This application claims the benefit of priority of U.S. Provisional Patent Application Serial No. 60/151,863, entitled "Additional Sutureless Anastomosis Embodiments," filed Sep. 1, 1999, the entirety of which is hereby incorporated by reference. Furthermore, this application is related to U.S. patent application Ser. No. 09/329,503, entitled "Sutureless Anastomosis Systems", filed Jun. 10, 1999; U.S. patent application Ser. No. 09/329,504, entitled "Thermal Securing Anastomosis Systems", filed Jun. 10, 1999; U.S. Provisional Patent Application Serial No. 60/111,948, entitled "Bypass Graft Positioning and Securing System", filed Dec. 11, 1998; U.S. patent application Ser. No. 08/932,566, entitled "Radially Expanding Prostheses and Systems for their Deployment," filed Sep. 19, 1997; U.S. Pat. No. 5,989,276 to Houser et al. Each of the foregoing is incorporated herein by reference in its entirety.

FIELD OF THE INVENTION

This invention relates to devices for deploying and securing the ends of bypass grafts designed to provide a fluid flow passage between at least two host vessel regions (or other tubular structure regions). More particularly, the invention relates to bypass grafts that are secured at target host vessel locations, thereby producing a fluid flow passage from the first host vessel location through the bypass graft and to the second host vessel location. The bypass grafts and deployment systems of the invention do not require stopping or re-routing blood flow to perform an anastomosis between a bypass graft and a host vessel. Accordingly, this invention describes sutureless anastomosis systems that do not require cardiopulmonary bypass support when treating coronary artery disease.

Current techniques for producing anastomoses during coronary artery bypass grafting procedures involve placing the patient on cardiopulmonary bypass support, arresting the heart, and interrupting blood flow to suture, clip, or staple a bypass graft to the coronary artery and aorta; cardiopulmonary bypass support is associated with substantial morbidity and mortality. The embodiments of the invention position and secure bypass grafts at host vessel locations without having to stop or re-route blood flow. Accordingly, the embodiments of the invention do not require cardiopulmonary bypass support and arresting the heart while producing anastomoses to the coronary arteries. In addition, the embodiments of the invention mitigate risks associated with suturing, clipping, or stapling the bypass graft to the host vessel(s); namely, bleeding at the attachment sites and collapsing of the vessel around the incision point.

The invention addresses vascular bypass graft treatment regimens requiring end-end anastomoses and end-side anastomoses to attach bypass grafts to host vessels. The scope of the invention includes improvements to the systems used to position and secure bypass grafts for treating vascular diseases such as atherosclerosis, arteriosclerosis, fistulas, aneurysms, occlusions, and thromboses. The improvements to the bypass grafts and delivery systems of the invention also aid in attaching the ends of ligated vessels, replacing vessels harvested for bypass grafting procedures (e.g. radial artery), and re-establishing blood flow to branching vessels which would otherwise be occluded during surgical grafting procedures (e.g., the renal arteries during abdominal aortic aneurysm treatment). In addition, the invention addresses other applications such as, but not limited to, producing arterial-to-venous shunts for hemodialysis patients, bypassing lesions and scar tissue located in the fallopian tubes causing infertility, attaching the ureter to the kidneys during transplants, and treating gastrointestinal defects (e.g. occlusions, ulcers, obstructions, etc.).

BACKGROUND OF THE INVENTION

Stenosed blood vessels cause ischemia potentially leading to tissue infarction. Conventional techniques to treat partially or completely occluded vessels include balloon angioplasty, stent deployment, atherectomy, and bypass grafting.

Coronary artery bypass grafting (CABG) procedures to treat coronary artery disease have traditionally been performed through a thoracotomy with the patient placed on cardiopulmonary bypass support and using cardioplegia to induce cardiac arrest. Cardiac protection is required when performing bypass grafting procedures associated with prolonged ischemia times. Current bypass grafting procedures involve interrupting blood flow to suture or staple the bypass graft to the host vessel wall and create the anastomoses. When suturing, clipping, or stapling the bypass graft to the host vessel wall, a large incision is made through the host vessel and the bypass graft is sewn to the host vessel wall such that the endothelial layers of the bypass graft and vessel face each other. Bypass graft intima-to-host vessel intima apposition reduces the incidence of thrombosis associated with biological reactions that result from blood contacting the epithelial layer of a harvested bypass graft. This is especially relevant when using harvested vessels that have a small inner diameter (e.g., $\leq 2$ mm).

Less invasive attempts for positioning bypass grafts at target vessel locations have used small ports to access the anatomy. These approaches use endoscopic visualization and modified surgical instruments (e.g., clamps, scissors, scalpels, etc.) to position and suture the ends of the bypass graft at the host vessel locations. Attempts to eliminate the need for cardiopulmonary bypass support while performing CABG procedures have benefited from devices that stabilize the motion of the heart, retractors that temporarily occlude blood flow through the host vessel, and shunts that re-route the blood flow around the anastomosis site. Stabilizers and retractors still require significant time and complexity to expose the host vessel and suture the bypass graft to the host vessel wall. Shunts not only add to the complexity and length of the procedure, but they require a secondary procedure to close the insertion sites proximal and distal to the anastomosis site.

Attempts to automate formation of sutureless anastomoses have culminated into mechanical stapling devices. Mechanical stapling devices have been proposed for creating end-end anastomoses between the open ends of transected vessels. Berggren et al. propose an automatic stapling device for use in microsurgery (U.S. Pat. Nos. 4,607,637, 4,624,257, 4,917,090, and 4,917,091). This stapling device has mating sections containing pins that are locked together after the vessel ends are fed through lumens in the sections and everted over the pins. This stapling device maintains intima-to-intima apposition for the severed vessel ends but has a large profile and requires impaling the everted vessel wall with the pins. Sakura describes a mechanical end-end stapling device designed to reattach severed vessels (U.S. Pat. No. 4,214,587). This device has a wire wound into a zigzag pattern to permit radial motion and contains pins bonded to the wire that are used to penetrate tissue. One vessel end is everted over and secured to the pins of the end-end stapling device, and the other vessel end is advanced over the end-end stapling device and attached with the pins. Sauer et al. proposes another mechanical end-end device that inserts mating pieces into each open end of a severed vessel (U.S. Pat. No. 5,503,635). Once positioned, the mating pieces snap together to bond the vessel ends. These end-end devices are amenable to reattaching severed vessels but are not suitable to producing end-end anastomoses between a bypass graft and an intact vessel, especially when exposure to the vessel is limited.

Mechanical stapling devices have also been proposed for end-side anastomoses. These devices are designed to insert bypass grafts, attached to the mechanical devices, into the host vessel through a large incision and secure the bypass graft to the host vessel. Kaster describes vascular stapling apparatus for producing end-side anastomoses (U.S. Pat. Nos. 4,366,819, 4,368,736, and 5,234,447). Kaster's end-side apparatus is inserted through a large incision in the host vessel wall. The apparatus has an inner flange that is placed against the interior of the vessel wall and a locking ring that is affixed to the fitting. This locking ring contains spikes that penetrate into the vessel thereby securing the apparatus to the vessel wall. The bypass graft is itself secured to the apparatus in the everted or non-everted position through the use of spikes incorporated in the apparatus design.

U.S. Surgical has developed automatic clip appliers that replace suture stitches with clips (U.S. Pat. Nos. 5,868,761, 5,868,759, and 5,779,718). These clipping devices have been demonstrated to reduce the time required when producing the anastomosis but still involve making a large incision through the host vessel wall. As a result, blood flow through the host vessel must be interrupted while creating the anastomoses.

Gifford et al. provides end-side stapling devices (U.S. Pat. No. 5,695,504) that secure harvested vessels to host vessel walls maintaining intima-to-intima apposition. This stapling device is also inserted through a large incision in the host vessel wall and uses staples incorporated in the device to penetrate into tissue and secure the bypass graft to the host vessel.

Walsh et al. proposes a similar end-side stapling device (U.S. Pat. Nos. 4,657,019, 4,787,386, and 4,917,087). This end-side device has a ring with tissue-piercing pins. The bypass graft is everted over the ring; then, the pins penetrate the bypass graft thereby securing the bypass graft to the ring. The ring is inserted through a large incision created in the host vessel wall and the tissue piercing pins are used to puncture the host vessel wall. A clip is then used to prevent dislodgment of the ring relative to the host vessel.

The previously described end-side stapling devices require insertion through a large incision, which dictates that blood flow through the host vessel must be interrupted during the process. Even though these and other clipping and stapling end-side anastomotic devices have been designed to decrease the time required to create the anastomosis, interruption of blood flow through the host vessel increases the morbidity and mortality of bypass grafting procedures, especially during beating heart CABG procedures. A recent experimental study of the U.S. Surgical One-Shot anastomotic clip applier observed abrupt ventricular fibrillation during four of fourteen internal thoracic artery to left anterior descending artery anastomoses in part due to coronary occlusion times exceeding 90 seconds (Heijmen, et al. "A Novel One-Shot Anastomotic Stapler Prototype for Coronary Bypass Grafting on the Beating Heart: Feasibility in the Pig" *J Thorac Cardiovasc Surg.* 117:117–25; 1999).

A need thus exists for bypass grafts and delivery systems that are capable of quickly producing an anastomosis between a bypass graft and a host vessel wall without having to stop or re-route blood flow. These anastomoses must withstand the pressure exerted by the pumping heart and ensure blood does not leak from the anastomoses into the thoracic cavity, abdominal cavity, or other region exterior to the vessel wall.

SUMMARY OF THE INVENTION

The embodiments of the present invention provide improvements to sutureless anastomosis systems that enable a physician to quickly and accurately secure a bypass graft to a host vessel or other tubular body structure. In addition, the invention adapts the sutureless anastomosis systems to applications involving robotic surgery and minimally invasive surgical approaches that involve a thoracostomy. The delivery systems of the invention do not require stopping or re-routing blood flow while producing the anastomosis; current techniques require interrupting blood flow to suture, clip, or staple a bypass graft to the host vessel wall.

The fittings of the invention are intended to secure biological bypass grafts, obtained by harvesting vessels from the patient or another donor patient, or synthetic bypass graft materials, to a patient's host vessel. When using harvested vessels, the fitting embodiments must accommodate a variety of harvested vessel sizes and wall thicknesses. When using synthetic bypass graft materials, the fittings may be incorporated in the bypass graft design to eliminate the step of attaching the bypass graft to the fitting prior to deploying the bypass graft and fitting.

One aspect of the invention provides additional fitting embodiments designed to compress into a reduced diameter while attaching the bypass graft to the fitting and/or deploying the fitting through the delivery system. Once deployed, the compressible fittings of the invention expand towards their preformed geometry such that they exert radial force at the vessel attachment sites; this helps maintain the patency of the anastomosis.

Another aspect of the invention provides additional angled fittings designed to produce anastomoses between bypass grafts and host vessels such that the angle between the bypass graft and the host vessel reduces turbulent flow near the anastomosis. The angled fittings may also be designed compressible.

A further aspect of the invention involves loading sheaths to facilitate securing the bypass graft to the fittings of the invention, and inserting the bypass graft and fitting combination through the delivery system. The loading sheath also protects the bypass graft and fitting combination during insertion through the delivery sheath. One loading sheath embodiment enables compressing the end-side fitting into a reduced diameter to facilitate advancing the bypass graft over the fitting base prior to securing the bypass graft to the fitting using a retaining ring or other compression device.

The single motion delivery system of the invention enables inserting the fitting and bypass graft into the host vessel without having to interrupt blood flow through the host vessel. The single motion delivery system embodiment combines the tear-away sheath, plunger, dilating mechanism, and perforating mechanism described in U.S. patent application Ser. No. 09/329,503 into a single tool designed to deploy the fitting and bypass graft combination through the host vessel wall at the desired anastomosis site.

After securing the bypass graft to the host vessel, components of delivery system still residing around the attached bypass graft are configured to split or expand to form a gap so the entire delivery system may be removed from around the bypass graft. This facilitates attaching both ends of the bypass graft using the delivery system of the invention and removing the delivery system from around the intact bypass graft. The delivery system also protects the bypass graft during insertion through an opening into the host vessel.

Further features and advantages of the inventions will be elaborated in the detailed description and accompanying drawings.

BRIEF DESCRIPTION OF THE DRAWINGS

FIGS. 3A to 3C show an angled end-side fitting of the present invention.

FIG. 7D shows a tool of the present invention used to compress the loading sheath.

FIGS. 8A and 8B show a single motion delivery system of the present invention.

DETAILED DESCRIPTION OF THE INVENTION

Figure 1:
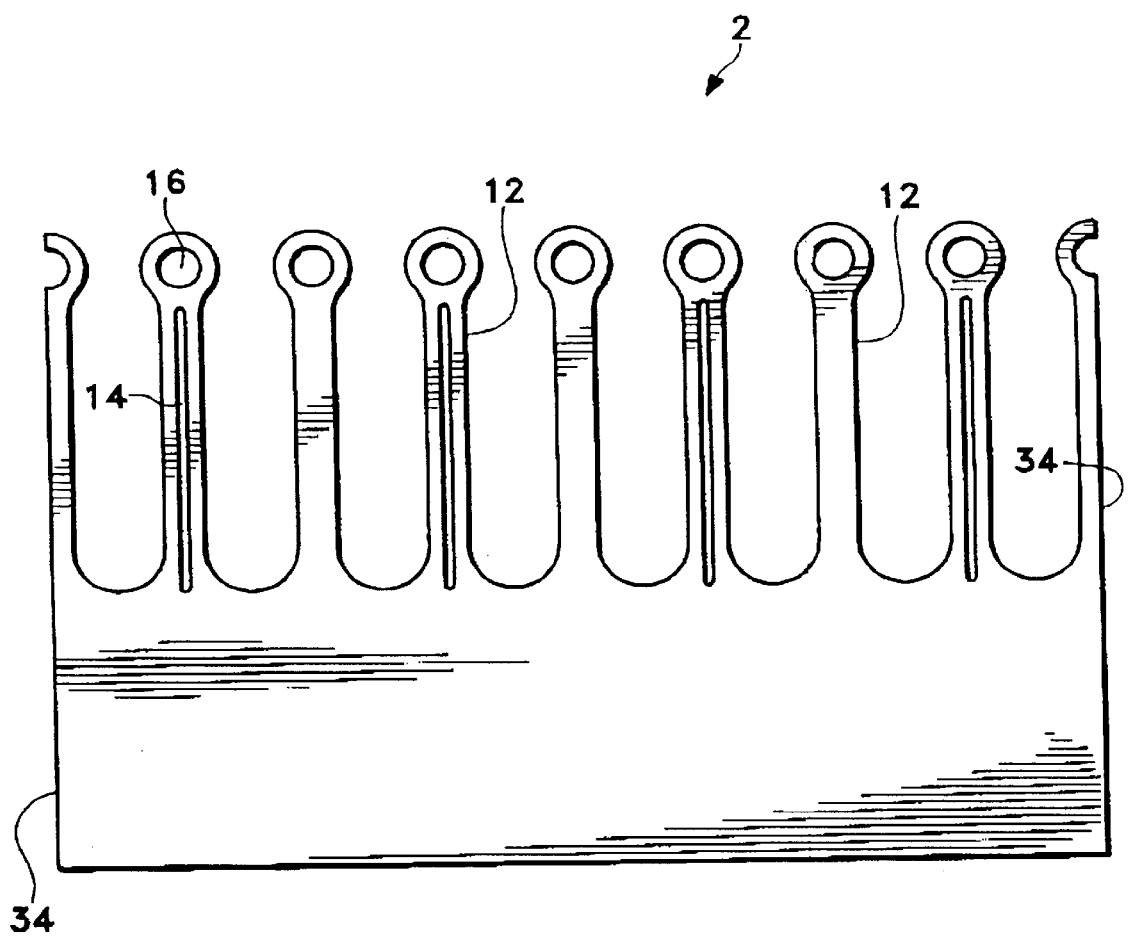
FIG. 1 shows a flattened split wall end-side fitting of the present invention containing petals having longitudinal slots and holes through the petals.

The fittings and delivery systems of the invention are intended to produce anastomoses between bypass grafts and host vessels to treat vascular abnormalities such as stenoses, thromboses, other occlusions, aneurysms, fistulas, or other indications requiring a bypass graft. The systems of the invention are also useful in bypassing stented vessels that have restenosed. Current approaches for treating stenosed stents have not been successful at safely and reliably removing the lesion and opening the vessel lumen. Therefore, the approach described by this invention, which produces a blood flow conduit around the stented lesion, mitigates concerns associated with damaging the stent or forming emboli while removing deposits attached to the stent. The embodiments of the invention also provide mechanisms to secure branching vessels to a replacement graft during surgical procedures in which the branching vessels would otherwise be occluded from blood flow (e.g., reattaching the renal arteries, mesenteric artery, celiac artery, and intercostal arteries during treatment of abdominal aortic aneurysms that are pararenal, suprarenal, or thoracoabdominal in classification). The embodiments of the invention also enable reattaching the left main artery and right coronary artery during aortic root replacement procedures.

The fitting and delivery system embodiments discussed in this invention are directly amenable to robotic surgery and less invasive (i.e., minimally invasive) surgery involving a thoracostomy or mini median sternotomy to access the anastomosis site. In particular, the fittings and delivery system embodiments of the invention enable automating the attachment of the bypass graft to the fitting, especially when considering the use of the loading sheath and/or single motion delivery sheath described below. In addition, the use of the delivery systems of the invention for deploying the fittings and bypass graft is significantly easier to automate than conventional suturing. Finally, the ability to advance the bypass graft and fitting combination along an axis defined by the delivery sheath facilitates automating the deployment of the bypass graft and fitting combination through the delivery sheath and into the host vessel.

Bypass Grafts

The bypass graft may be a synthetic graft material, harvested vessel, or other tubular body structure, depending on the indication for use. The harvested vessels may be an internal mammary artery, mesenteric artery, radial artery, saphenous vein or other body tubing. Harvested vessels may be dissected using newer minimally invasive, catheter-based techniques or standard surgical approaches. The end-side fittings in accordance with the invention are designed to attach bypass grafts to host vessels (or other tubular structures). The fittings used to position and attach such bypass grafts are extensions of the collet and grommet embodiments described in U.S. Pat. No. 5,989,276, and the fittings described in U.S. patent application Ser. No. 09/329, 503. The primary advantage of biological bypass grafts (e.g., harvested vessels) over currently available synthetic materials is the reduction in thrombosis especially when using small diameter (e.g., ≦2 mm) bypass grafts. However, the fittings and delivery systems of the invention are equally effective at positioning and securing all types of bypass grafts, biological and synthetic.

Synthetic bypass grafts may be manufactured by extruding, injection molding, weaving, braiding, or dipping polymers such as polytetrafluoroethylene (PTFE), expanded PTFE, urethane, polyamide, polyimide, nylon, silicone, polyethylene, collagen, polyester, composites of these representative materials, or other suitable graft material. These materials may be fabricated into a sheet or tubing using one or a combination of the stated manufacturing processes. The sides of sheet materials may be bonded using radio frequency (RF) energy, laser welding, ultrasonic welding, thermal bonding, sewing, adhesives, or a combination of these processes to form tubing. The synthetic bypass graft may be coated, deposited, or impregnated with materials, such as parylene, heparin solutions, hydrophilic solutions, or other substances designed to reduce thrombosis or mitigate other risks that potentially decrease the patency of synthetic bypass grafts.

The primary advantage of synthetic bypass graft materials is the ability to bond the bypass graft to the fittings prior to starting the procedure or incorporate the fittings into the bypass graft by injection molding or other manufacturing process. Currently, synthetic bypass grafts are indicated for blood vessels having medium and large diameters (e.g., >3 mm), such as peripheral vessels, tubular structures such as the fallopian tubes, or shunts for hemodialysis. However, medical device manufacturers such as Possis Medical, Inc. and Thoratec Laboratories, Inc. are evaluating synthetic bypass grafts for coronary indications. In this disclosure and the accompanying drawings, reference to bypass graft may pertain to either biological bypass grafts such as harvested vessels or synthetic bypass grafts, unless specifically stated.

As discussed in co-pending U.S. patent application Ser. No. 08/932,566 and U.S. Pat. No. 5,989,276, support members may be incorporated into the bypass graft. When using synthetic bypass grafts, the support members may be laminated between layers of graft material. The synthetic bypass graft encompassing support members may be fabricated by extruding, spraying, injection molding, or dipping a primary layer of graft material over a removable mandrel; positioning, winding or braiding the support members on the primary layer; and extruding, spraying, injection molding, or dipping a secondary layer over the graft material/support member combination. The support members may be fabricated from a metal, alloy (e.g., stainless steel or nickel titanium), or polymer (e.g., nylon or polyester); however, the support members preferably have a shape memory. Support members enhance the performance of the bypass graft by maintaining lumenal patency, offering flexibility and increasing the strength. Support members fabricated from memory elastic alloys exhibiting stress-induced martensitic characteristics, such as nickel titanium, further reinforce the bypass graft and/or vessel wall and prevent permanent deforming upon exposure to external forces. Such support members also permit compressing the bypass graft into a low profile during deployment through the host vessel wall. The support members urge the bypass graft to expand towards its preformed configuration after the constraining means (e.g., delivery system) is removed.

End-Side Fittings

The end-side fittings are constructed from a metal (e.g., titanium), alloy (e.g., stainless steel or nickel titanium), thermoplastic, thermoset plastic, silicone or combination of the aforementioned materials into a composite structure; other materials may alternatively be used. The fittings may be coated with materials such as parylene or other hydrophilic substrates that are biologically inert and reduce the surface friction. Alternatively, the fittings may be coated with heparin or thrombolytic substances designed to prevent thrombosis around the attachment point between the bypass graft and the host vessel. Alternatively, material such as platinum, gold, tantalum, tin, tin-indium, zirconium, zirconium alloy, zirconium oxide, zirconium nitrate, phosphatidyl-choline, or other material, may be deposited onto the fitting surface using electroplating, sputtering vacuum evaporation, ion assisted beam deposition, vapor deposition, silver doping, boronation techniques, a salt bath, or other coating process.

The fittings consist of one or more components designed to secure a bypass graft to the fitting and the fitting to the vessel wall to produce a fluid tight bond between the bypass graft and the host vessel. The fittings may be used to produce end-side anastomoses for medium and small diameter vessels (e.g., peripheral vessels and coronary vessels) where retrograde blood flow is essential, and end-side anastomoses for large diameter vessels (e.g., the aorta). The fittings and delivery systems described below may be modified to accommodate end-end anastomoses by eliminating the petals from the design.

Retaining rings may be used to secure the bypass graft to the end-side fitting. The retaining rings may be fabricated from a metal, alloy, thermoplastic material, thermoset, or composite. The retaining ring must permit approximately 30% enlargement in diameter without becoming permanently deformed. One retaining ring embodiment is a preshaped member wound beyond a single turn and having radiused edges and ends. One representative fabrication process for the preshaped retaining ring involves forming the raw material into a desired geometry and exposing the material to sufficient heat to anneal the material into this predetermined shape. This process applies to metals, alloys (e.g. nickel titanium) and polymers. The preshaped retaining ring configuration is expanded thereby enlarging the diameter of the retaining ring. Once the retaining ring is positioned, the force causing the retaining ring to enlarge is removed causing the retaining ring to return towards its preformed shape thereby compressing the bypass graft against the fitting.

The embodiments of the invention involve attaching the bypass graft around the exterior of the fitting. The bypass graft is secured around the base of fittings using retaining rings, described above. The bypass graft is advanced over the exterior of the fitting and is secured with a retaining ring, suture (not shown), or staples (not shown). The base of the fitting and/or the retaining ring may contain barbs designed to lock the bypass graft to the base of the fitting. Alternatively, notches may be fabricated in the base of the fitting and adapted to accept the retaining ring. The barbs or notches reinforce the compression fit between the bypass graft and the base of the fitting, achieved by positioning retaining rings in the indents defined by the barbs or notches. The base of the fitting and the retaining ring may alternatively be configured to match, once deployed, especially when the fitting and retaining ring are compressible. The base of the compressible fitting 4 defines spaces 32 (shown in FIG. 2A); the retaining ring may be designed to position extensions of the retaining ring (matching those of the fitting) within these spaces further locking the retaining ring to the fitting and enhancing the bond between the bypass graft and the fitting.

One end-side fitting embodiment, shown in FIG. 1, is fabricated by cutting a sheet of fitting material into the desired pattern and thermally forming fitting 2 around a mandrel. Sides 34 of fitting 2 may be bonded to form an enclosed tube or may be formed with a gap between the sides to enable compressing fitting 2 into a reduced diameter for positioning the bypass graft over the base of the fitting and for inserting the fitting through a delivery system having a diameter less than the expanded diameter of the fitting. Such compressible fittings also facilitate sizing issues since they accommodate a wide range of bypass graft sizes. The pattern of this end-side fitting sheet stock may be fabricated by chemical etching, electrondischarge machining (EDM), or laser drilling the pattern of petals 12, slots 14, and holes 16 as shown; other manufacturing processes may alternatively be used. The end-side fitting is wrapped around a mandrel having the desired resting cross-sectional profile and the end-side fitting is heated until it assumes this configuration. If the sides are to be bonded, spot welding, laser welding, or other manufacturing process may be employed. Alternatively, the fitting may be fabricated from a tubular metal material using chemical etching, EDM, laser drilling, or other manufacturing process to form the desired pattern. Again, the fitting may be formed into a tube or a gap may be created to make the fitting compressible. When forming the resting configuration of the compressible, split wall end-side fitting, a gap is retained between opposite sides. The gap between sides 34 of the fitting permits compressing the end-side fitting into a reduced diameter which facilitates positioning the bypass graft over the base of the fitting and/or advancing the fitting through a delivery system having an inner diameter less than the outer diameter of the fitting in its expanded, resting configuration. In addition, this helps size a single fitting configuration to accommodate a wide range of bypass graft sizes.

Figure 2A:
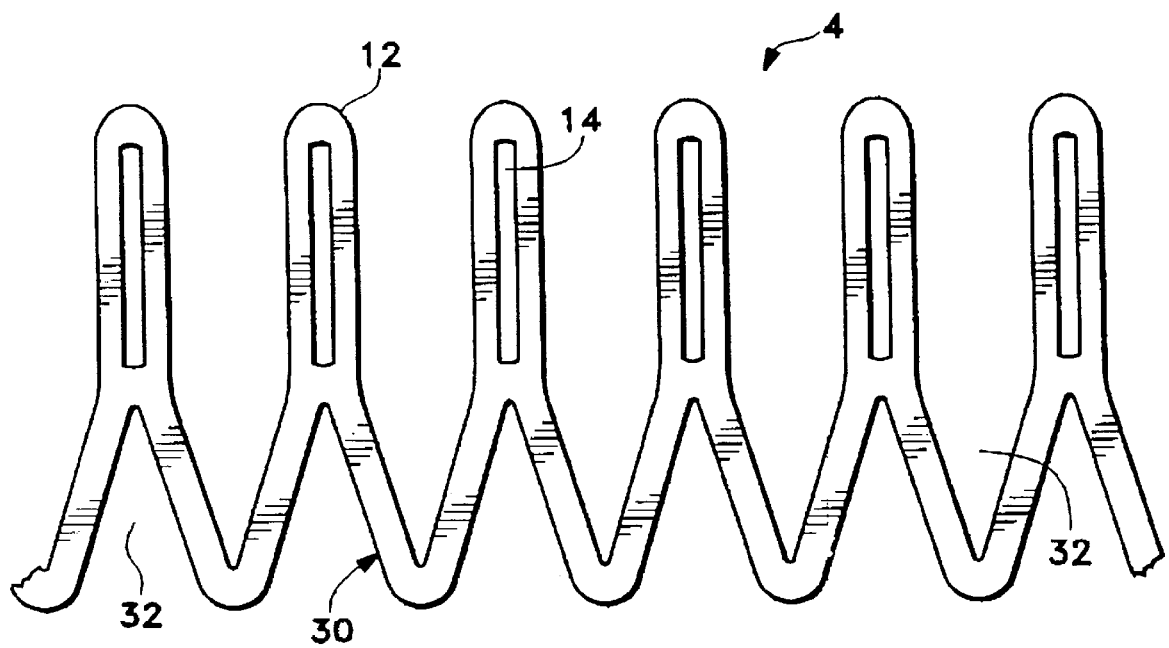
FIG. 2A shows a flattened compressible end-side fitting of the present invention containing petals.
Figure 2B:
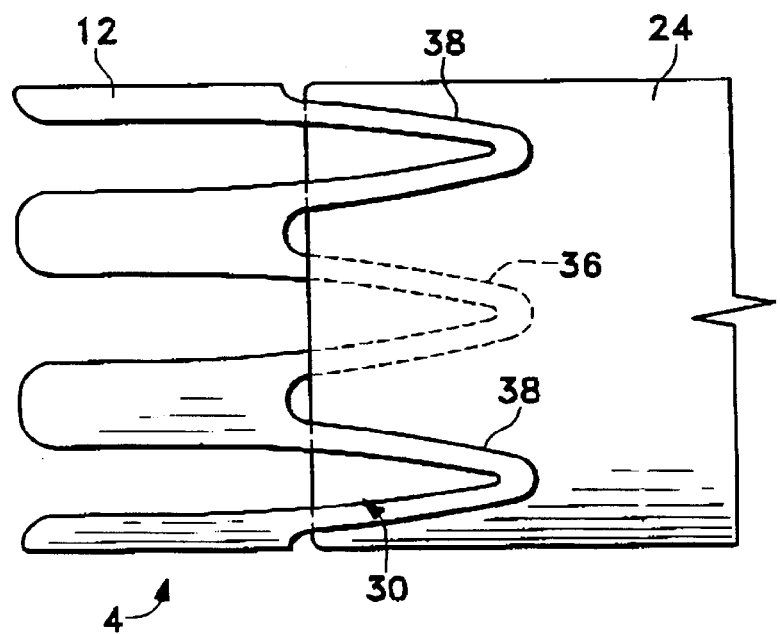
FIG. 2B shows a compressible end-side fitting of the present invention with a bypass graft secured between compressible extensions of the fitting base.

Another end-side fitting that permits compressing into a reduced diameter while placing the bypass graft over the base 30 of the fitting is shown in FIGS. 2A and 2B. The embodiment 4 shown in FIG. 2A is depicted in a flat profile; in operation, the base of the fitting is enclosed into a tube having a desired cross-sectional geometry (e.g. circular, elliptical, etc.). This fitting 4 may be fabricated as a sheet with opposite sides bonded using a secondary manufacturing process (e.g., spot welding, laser welding, etc.) to enclose the base; this fitting may also be fabricated as a sheet and thermally formed into a split wall fitting having a gap between fitting sides 34. Alternatively, the fitting may be fabricated from a tube having the desired cross-sectional geometry (e.g. circular, elliptical, other). As previously described, the desired pattern of petals, spaces, slots, and holes may be fabricated using laser drilling, EDM, chemical etching, milling, or other manufacturing process.

Figure 2C:
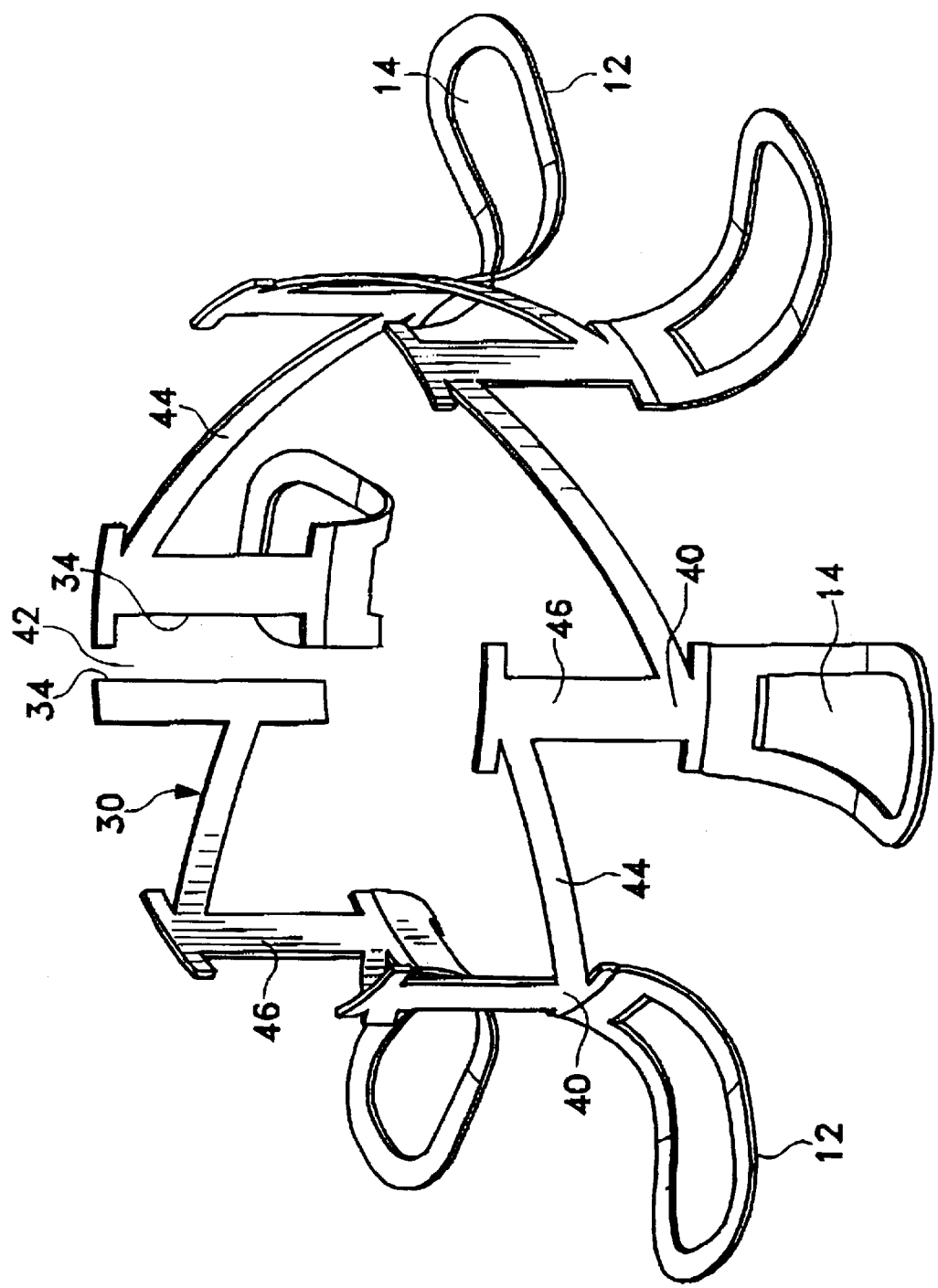
FIG. 2C shows an alternative compressible end-side fitting embodiment of the present invention.

FIG. 2C shows another compressible end-side fitting embodiment 4. The illustrated embodiment is thermally formed as a split wall fitting with gap 42 between opposite sides 34. To compress this split wall fitting (as well as the other split wall embodiments), the sides are caused to overlap forming a scroll with the fitting. The manufacturing processes and design for all split wall end-side fitting embodiments are the same as that described for the split wall graft and stent disclosed in U.S. patent application Ser. No. 08/932,566.

The end-side fitting 4 shown in FIG. 2C may alternatively be fabricated into an enclosed tube by bonding sides 34 together or forming the fitting from a tube without fabricating gap 42 in the fitting. This embodiment is still compressible because links 44 preserve the ability to compress the fitting into a reduced diameter or expanding into an enlarged diameter. Links 44 shown in FIG. 2C connect proximal petal ends 40 to adjacent base members 46. The links are formed at an angle between 10 and 80 degrees relative to base members 46. The width, length, thickness, and the angle of the links are designed to provide maximum compression or expansion and preserve the radial stiffness of fitting base 30. This is especially important since base 30 must keep the opening through the host vessel wall patent. Additional links may be included to configure base 30 into a mesh as opposed to an "N" as shown in FIG. 2C. The additional links provide the benefit of increasing the radial stiffness of the fitting base.

Figure 2D:
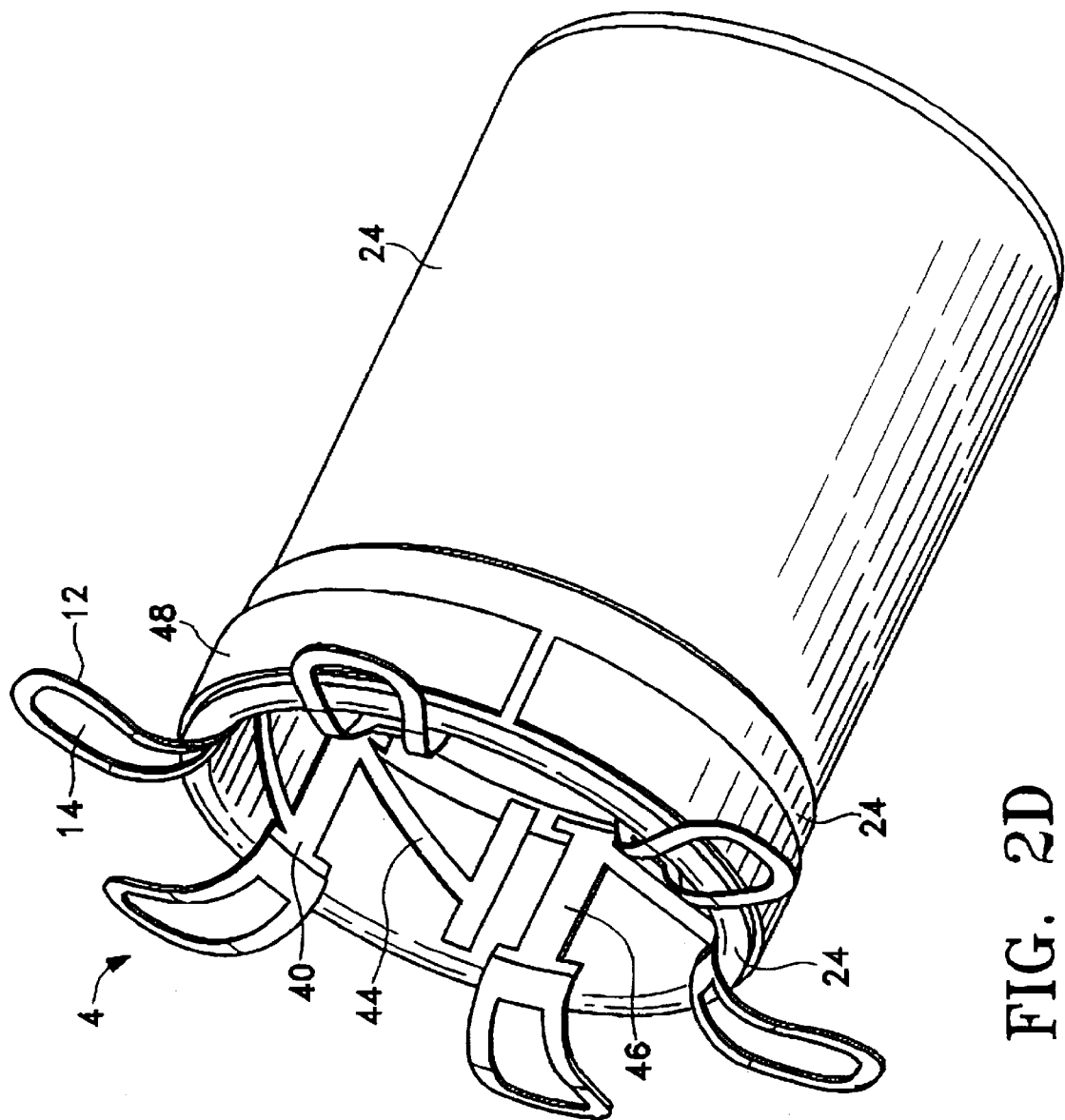
FIG. 2D shows a bypass graft of the present invention attached to the compressible end-side fitting embodiment of FIG. 2C.

FIG. 2D shows a bypass graft 24 attached to the compressible end-side fitting 4 shown in FIG. 2C and discussed above. Base 30 of the end-side fitting 4 is compressed into a reduced diameter while the bypass graft is advanced over the base. Once positioned, a retaining ring 48 (also compressible and expandable) is positioned over the bypass graft-to-base interface and the external force compressing the base is removed, allowing the base to return towards its resting configuration. The bypass graft becomes compressed between base 30 on the interior surface of bypass graft 24 and retaining ring 48 on the external surface. The retaining ring 48 shown in FIG. 2D is fabricated from a memory elastic material thermally formed into a ring having a gap between opposite sides. Of course, other retaining ring designs may be used, including those disclosed in U.S. patent application Ser. No. 09/329,503 and U.S. Provisional Patent Application Serial No. 60/111,948.

This compressible end-side fitting 4 (as well as the other embodiments) may be expanded into an enlarged diameter so the base of the fitting may be placed over a bypass graft everted over a central member. When the external force expanding the fitting is removed, the end-side fitting compresses the bypass graft against the central member, thus securing the bypass graft to the fitting. In addition, the base of the fitting (as well as the petals if desired) may be covered with a fluid-tight compliant material such as silicone, urethane, or other material. The fitting base coating may be fabricated by dipping, injection molding, or other manufacturing process. This covering permits compressing and expanding the base of the fitting but improves leak resistance of the anastomosis and isolates the cut end of the bypass graft from blood. These aspects are discussed in U.S. patent application Ser. No. 09/329,503 and U.S. Provisional Patent application Serial No. 60/111,948.

The petals 12 in these fitting embodiments of the invention are shown straight (i.e., at an angle of zero degrees from the base of the fitting). While manufacturing, the petals are thermally formed at an angle between 30 and 150 degrees from the base of the fitting such that the petals contact the interior surface of the host vessel once the fitting is inserted through the host vessel wall. Petals 12, having an angle between 30 and 150 degrees from the base of the fitting in their resting orientation, also compress into a reduced outer diameter during deployment through the delivery system and expand towards their resting configuration once deployed inside the host vessel. The number of petals incorporated in the end-side fitting design depends on the size of the bypass graft and the size of the host vessel. In this illustrated embodiment of FIG. 2, six petals are used. After advancing the fitting through the delivery system and past the vessel wall, the fitting is advanced beyond the end of the delivery system and is no longer constrained by the confines of the delivery system such that petals 12 may expand towards their resting configuration. Then, the bypass graft and fitting combination is gently retracted to engage the interior vessel wall with the petals. For mechanical securing, a compression ring (not shown) is advanced over the fitting thereby compressing the vessel wall against the petals 12 of the end-side fitting.

The thickness, length, and width of the petals determine their spring characteristic and stiffness. Petals having a wall thickness of between approximately 0.002" and 0.005", a width between approximately 0.015" and 0.050", and a length between 2 mm and 10 mm are capable of being readily advanced through the delivery sheath when the petals are compressed forward into a reduced diameter. Petals having these dimensions also exhibit sufficient spring force to secure the end-side fitting to a host vessel wall, even without a compression ring.

As an example, petals having a wall thickness of 0.007", a width of 0.060", and a length between 2 mm and 5 mm were compressed into a reduced diameter and advanced through a delivery sheath; these fitting petals hindered advancement of the fitting through the delivery sheath because the edges of the petals caught on the inner surface of the delivery sheath.

At least one of the petal parameters may be modified to mitigate the insertion difficulties. For example, when slots having a width of 0.006" were created through petals having a wall thickness of 0.007", a width of 0.020", and a length of 5 mm, the petals were readily advanced through the delivery sheath. In addition, these petals exhibited sufficient spring force to secure the end-side fitting to a host vessel wall, even without a compression ring.

Petals fabricated from memory elastic materials as described above are preferred over deformable petals because they maintain their shape when exposed to external forces and do not require an expansion device to position the petals into contact with the host vessel wall. However, petals of the end-side fitting may be fabricated from a deformable material such as stainless steel, which can be expanded into position using a dilator or balloon. These petals expand into contact with the host vessel wall as the dilator or balloon separates the inner surfaces of the petals. Even though using deformable materials is not the preferred choice for the fittings, many of the embodiments (e.g., the delivery system) apply to the use of deformable fittings.

The end-side fitting may also be configured to secure the bypass graft to the fitting without the need for a retaining ring. As shown in FIG. 2B, adjacent base extensions may be separated in opposite directions while the bypass graft is inserted over inner extensions 36 and under outer extensions 38. Once the bypass graft is positioned, the external force separating the extensions is removed, causing the extensions to return towards their preformed configuration and compressing the bypass graft between the adjacent extensions. The distance between the inner and outer extensions is preferably short so to increase the compressive forces exerted against the bypass graft and to produce a stronger bond between the fitting and the bypass graft.

The end-side fittings may incorporate tabs 22 (as shown in FIGS. 3A and 3B), or a threaded mechanism (not shown) with which to secure a compression ring to the end-side fitting. The tabs in FIGS. 3A and 3B are shown flush with the base of the fitting. In operation, the tabs are preformed so they protrude radially from the base of the fitting to provide an mechanism to secure the compression ring, once positioned distal to the tabs. The tabs are also formed from a memory elastic material so they have a spring characteristic, permitting the tabs to be compressed into a reduced diameter during deployment. The tabs are compressed to facilitate inserting the base of the fitting through the delivery system and expand towards their preformed configuration once the fitting is positioned and the external force compressing the tabs is removed. The tabs are fabricated by creating the desired pattern in the fitting material by laser drilling, chemical etching, EDM, or other manufacturing process, whether fitting is fabricated as a sheet or tube. Alternatively, tabs may be fabricated as a separate component and bonded to the fitting by spot welding, laser welding, or other manufacturing process.

The compression ring is alternatively locked in place using adhesives, sutures, or other attachment means to secure the compression ring in place. The compression ring of the illustrated embodiment incorporates two components: an outer, flexible covering designed to produce a fluid tight seal and prevent damaging the vessel wall by excess compression, and a central, memory elastic material used to maintain the position of the compression ring relative to the vessel wall and prevent permanent deformation of the compression ring when expanded into an enlarged diameter for positioning around the base of the fitting. The compression ring is preferably fabricated as a partial coil with approximately one turn. This compression ring produces an opening upon expansion, which permits advancing the compression ring over the side of the end-side fitting. This eliminates the need to preload the compression ring over the bypass graft. This compression ring also produces a secure, fluid tight bond between host vessel walls and compressible end-side fittings whose outer diameter is determined by the size of the bypass graft.

FIGS. 3A to 3C show another end-side fitting used to produce an end-side anastomosis. In this embodiment, the fitting 6 incorporates petals 12 that compress into a reduced outer diameter while being advanced through a delivery system and extend radially outward once deployed into the host vessel interior. In this embodiment, the bypass graft is advanced over the outside of the fitting 6 and is secured using a retaining ring (not shown). Alternatively, the fitting is laminated between layers of synthetic bypass graft material. A compression ring (not shown) is advanced over the fitting, after deploying fitting 6 into the interior of the vessel, and is used to compress the host vessel wall against the deployed petals of the fitting. As previously discussed, tabs 22 on the fitting help prevent axial dislodgement of the compression ring better ensuring a permanent bond between the fitting and the host vessel wall.

Figure 4A:
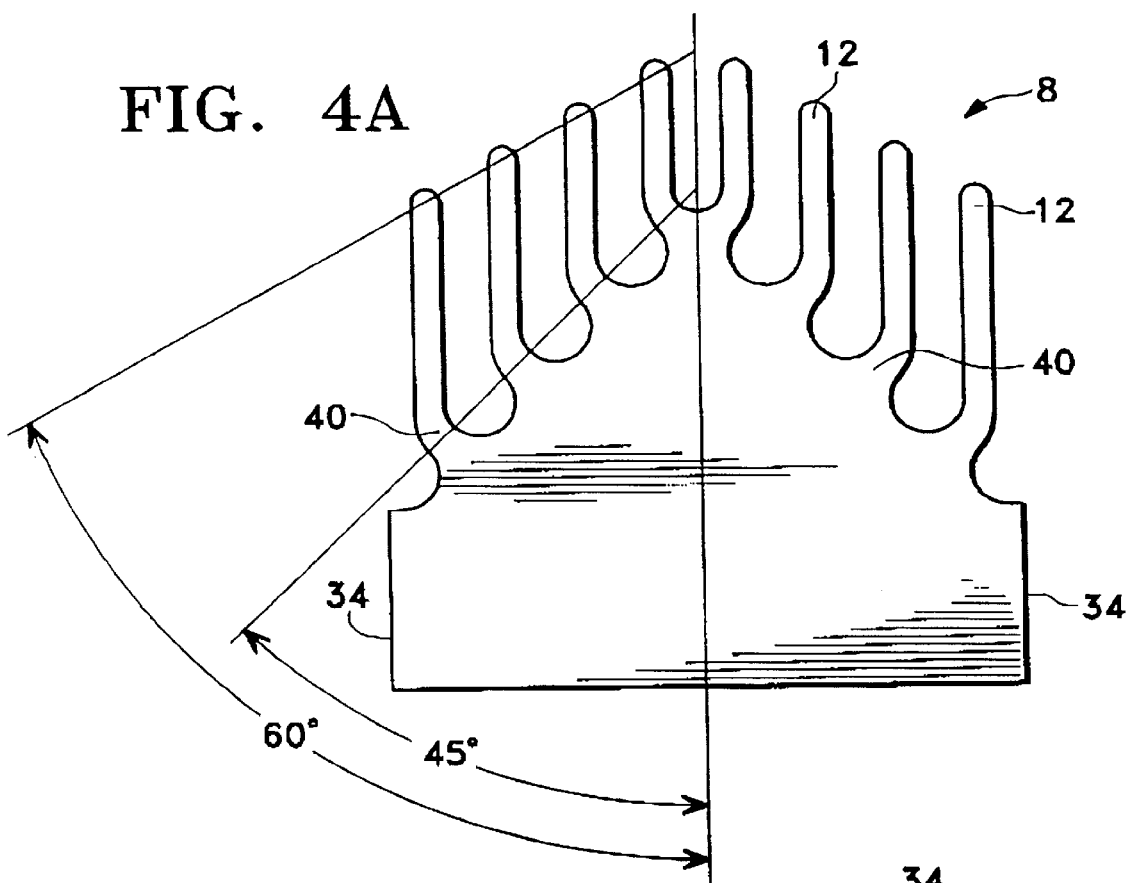
FIG. 4A shows an angled split wall end-side fitting of the present invention.
Figure 4B:
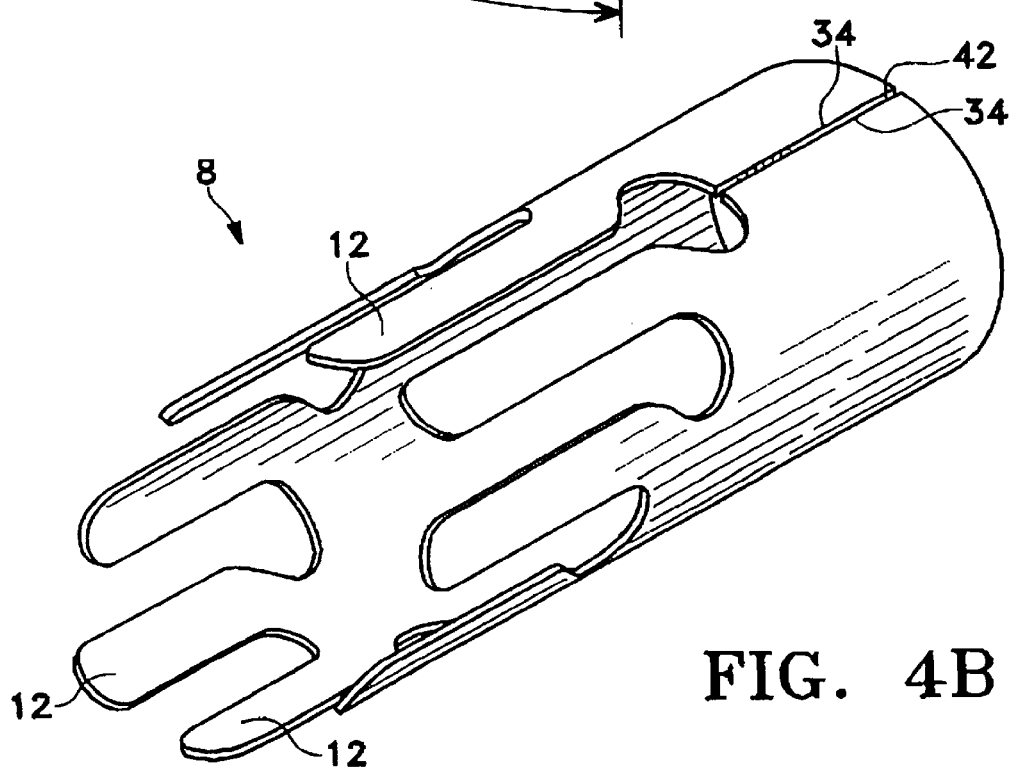
FIG. 4B shows an angled split wall end-side fitting of the present invention formed into its resting configuration.
Figure 5A:
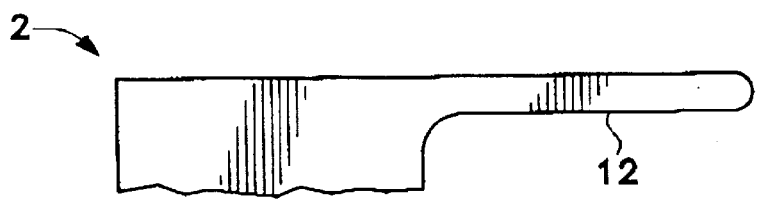
FIGS. 5A to 5F show various petal embodiments of the present invention.
Figure 5B:
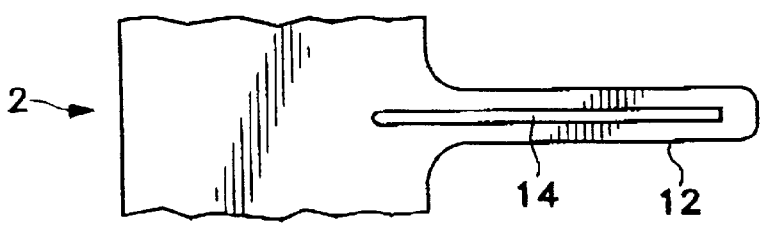
Figure 5C:
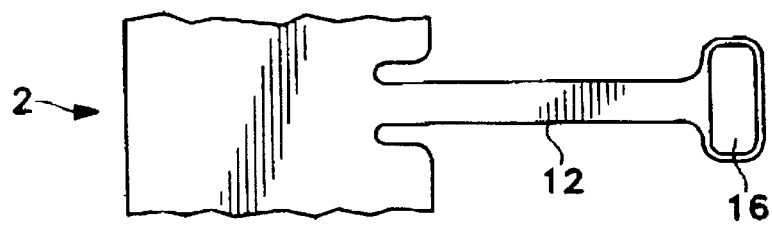
Figure 5D:
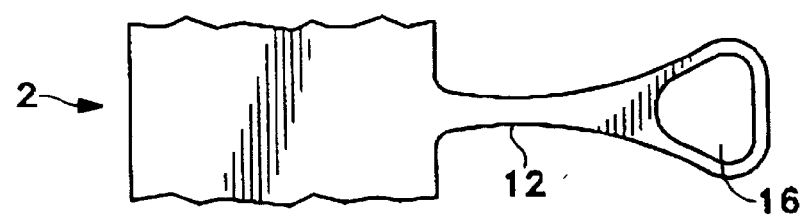
Figure 5E:
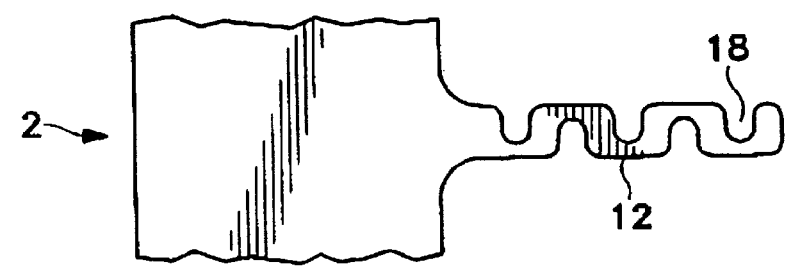
Figure 5F:
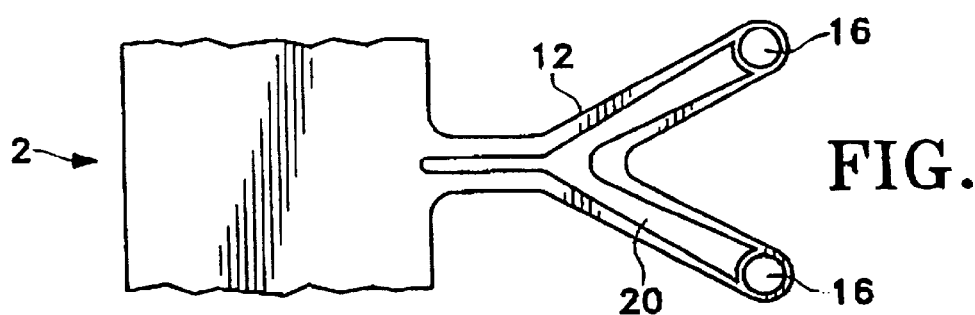
Figure 6A:
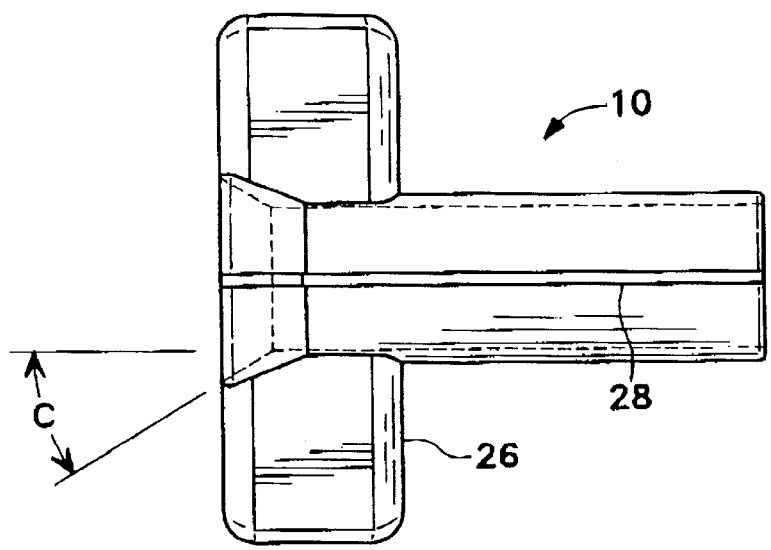
FIGS. 6A to 6D show a loading sheath of the present invention capable of splitting along at least one side.
Figure 6B:
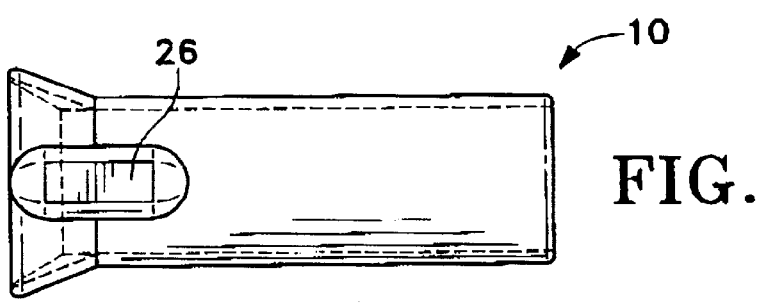
Figure 6C:
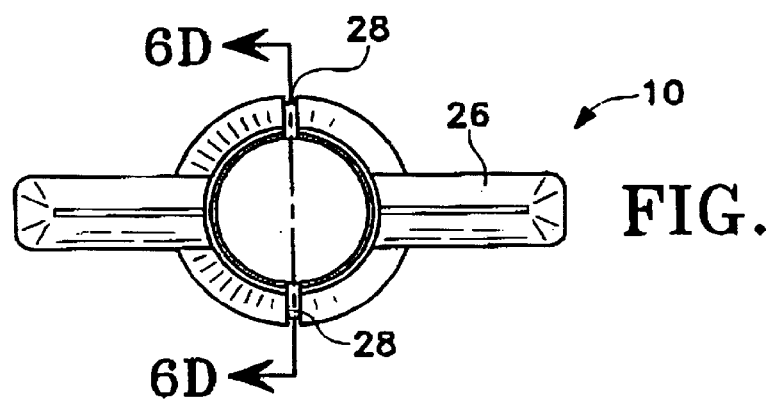
Figure 6D:
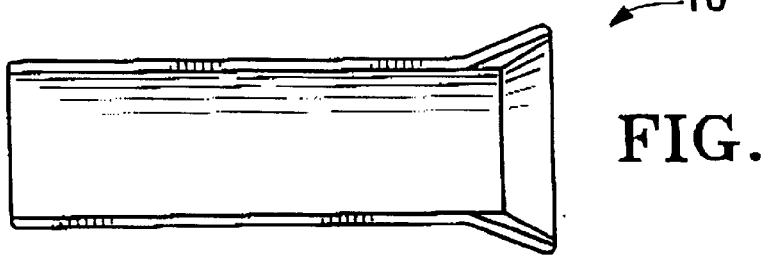

As shown in FIGS. 3A to 3C, the end-side fittings may be configured to produce an angle (A) between the bypass graft and the interior of the host vessel. As shown in FIG. 3B, the locations of the proximal petal ends 40 determine the angle fitting 6 produces between the bypass graft and the host vessel. This angle may be created between 30 and 90 degrees. This angled end-side fitting 6 may be fabricated from a tubing as shown in FIGS. 3A to 3C using manufacturing process previously described for forming patterns of petals, slots, holes, and tabs. Alternatively, as shown in FIG. 4A, the angled end-side fitting may be fabricated from a sheet material. Sides 34 of fitting 8 may be bonded together to form a tube having a desired cross-sectional geometry (e.g. circular, elliptical, etc.). Alternatively, the sheet material may be thermally formed into a desired cross-sectional geometry having a gap 42 between the sides 34 of the sheet material, as shown in FIG. 4B. This transforms the fitting into a compressible split wall end-side fitting 8 capable of accommodating a range of bypass graft sizes. The angled end-side fitting may alternatively be fabricated as an enclosed tube with the base permitting compression into a reduced outer diameter or expansion into an enlarged inner diameter (for situations where the fitting compresses an everted bypass graft against a central tube). To accomplish this the compressible end-side fitting shown in FIG. 2A would be modified such that the proximal petal ends form an angle between the bypass graft and the interior of the host vessel.

Another important feature is the incorporation of holes 16, longitudinal slots 14, lateral slots 18, and complex slots 20 in the petals of the end-side fitting, as shown in FIGS. 5A to 5F. The holes and slots may be fabricated by laser drilling, chemical etching, EDM, milling, or other manufacturing process. As previously described, the holes and slots increase the axial and/or radial flexibility of the petals enabling the use of thicker petals and producing petals that exhibit better stress-strain characteristics preventing petal fracture. The incorporation of holes and slots in the fitting also provide a surface to encourage neointimal cell growth. The fitting may alternatively be covered with a porous material, such as collagen, fibrinogen, gelatin, and urethane, to define a surface characterized by holes and slots. This is especially important for fitting surfaces exposed to blood flow.

The compressible fittings described above cover a wide range of bypass graft sizes with a few discrete fitting sizes. A color-coded sizing chart (not shown) facilitates identifying and choosing the appropriate fitting to match the size of the bypass graft. The bypass graft is gently flattened and the width of the flattened end of the bypass graft to be secured to the fitting is measured. This length identifies a nominal bypass graft diameter on the sizing chart, which falls in the range of diameters a particular fitting covers. This color-coding scheme decreases errors in choosing the wrong fitting size and reduces the time required to choose the fitting size.

The fittings in accordance with this invention may be used in any combination to secure bypass grafts at discrete vessel locations. In addition, synthetic and biological bypass grafts may also be used in any combination with the graft fittings to produce passages around vascular abnormalities during a particular procedure.

Delivery Systems

Conventional anastomosis techniques require a relatively large incision through the vessel wall and use sutures, commercially available clips, or stapling devices to bond the end of the bypass graft to the exposed edges of the vessel wall. In certain cases, the structural integrity of the vessel wall may be weakened, causing the vessel to collapse at the anastomosis site, especially when the bypass graft is not appropriately aligned to the host vessel incision. Therefore, the delivery system embodiments of the invention are designed to quickly access the host vessel through a small puncture in the vessel wall. As such, the delivery systems are designed to prevent excess blood loss when accessing the host vessel and deploying the bypass graft and fitting combination, thereby eliminating the need to stop or re-route blood flowing through the host vessel. This approach also improves the leak resistance around the fitting due to elastic compression of the vessel wall around the fitting and automatically aligns the bypass graft to the host vessel wall at the anastomosis site.

For surgical applications, physicians are able to access the anastomosis sites from the exterior surface of the host vessel(s). The delivery system of the surgical approach must permit removal after both ends of the bypass graft are secured and the delivery system resides around the attached bypass graft. The delivery mechanism uses conventional intravenous access techniques to produce an opening through the host vessel wall. This technique of inserting a sheath into a vessel over a dilating mechanism and perforating mechanism is commonly used by physicians when performing the Seldinger technique during catheterization procedures or inserting intravenous catheters into veins for withdrawal of blood or introduction of medicines. The sheath and dilating mechanism of the delivery system may be constructed from polyethylene or other polymers that may be extruded or molded into a tube. The sheath and dilating mechanism of the delivery mechanism may incorporate a braided layer laminated between two polymer layers to resist kinking and improve the column strength and torque response. A taper and radius may be formed in the components of the delivery mechanism by thermally forming the tubing into the desired shape. In addition, the components of the delivery system may incorporate a softer distal tip fabricated by thermally bonding a short section of lower durometer tubing to the sheath or tapering the thickness of the sheath tubing.

To prevent the backflow of blood through the sheath, hemostatic valves are used. The hemostatic valves prevent blood leakage but permit insertion of a device such as a fitting with an attached bypass graft through the sheath. The hemostatic valve of the delivery system of the invention also incorporates a mechanism to split and remove from around the bypass graft. To accomplish this, the hemostatic valve is formed as two halves attached to the hub of the sheath which, when split along at least one side, causes the hemostatic valve halves to separate. To incorporate a splitting mechanism in the sheath, grooves, series of perforations, or slits are incorporated in the sheath tubing and hub member. The grooves, series of perforations, or slits may be fabricated while injection molding or otherwise manufacturing the sheath tubing and/or hub, or may be formed in the assembled sheath by laser drilling, milling, EDM, or other manufacturing process.

The petals of the end-side fitting must be compressed forward into a reduced outer diameter while inserting the end-side fitting, with bypass graft attached, through the sheath of the delivery system. To facilitate this step, a loading sheath 10 (shown in FIGS. 6A to 6D) may be used to open the hemostatic valve and provide a smooth transition from the interior of the loading sheath to the interior of the delivery system sheath. Loading sheath 10 also protects the bypass graft while inserting through the delivery system sheath. The proximal end of loading sheath 10 forms a funnel with angle C, having a gradual transition into the loading sheath tubing, to facilitate inserting the compressed petals of the end-side fitting into the interior of the loading sheath. The delivery sheath also preferably has a gradual proximal end transition from the hub to the sheath interior to facilitate advancing the end-side fitting from the loading sheath and into the delivery sheath without catching the petals against the sheath tubing. The angle C of the transition from the proximal end of the loading sheath (or delivery sheath hub) to the sheath tubing is preferably between 15 and 60 degrees; angle C is 30 degrees in the illustrated embodiment. The loading sheath 10 also incorporates grooves 28, series of perforations, or slits to facilitate splitting the loading sheath along at least one side for removal from around the bypass graft. Hub extensions 26 on the loading sheath facilitate this splitting. As hub extensions 26 are separated, a tear along groove 28, series of perforations, or slit develops which may be split further to form an opening through at least one side of loading sheath 10. Preferably, two opposite grooves 28, series of perforations, or slits are formed in the loading sheath to enable separating split loading sheath 10 into two distinct pieces.

Figure 7A:
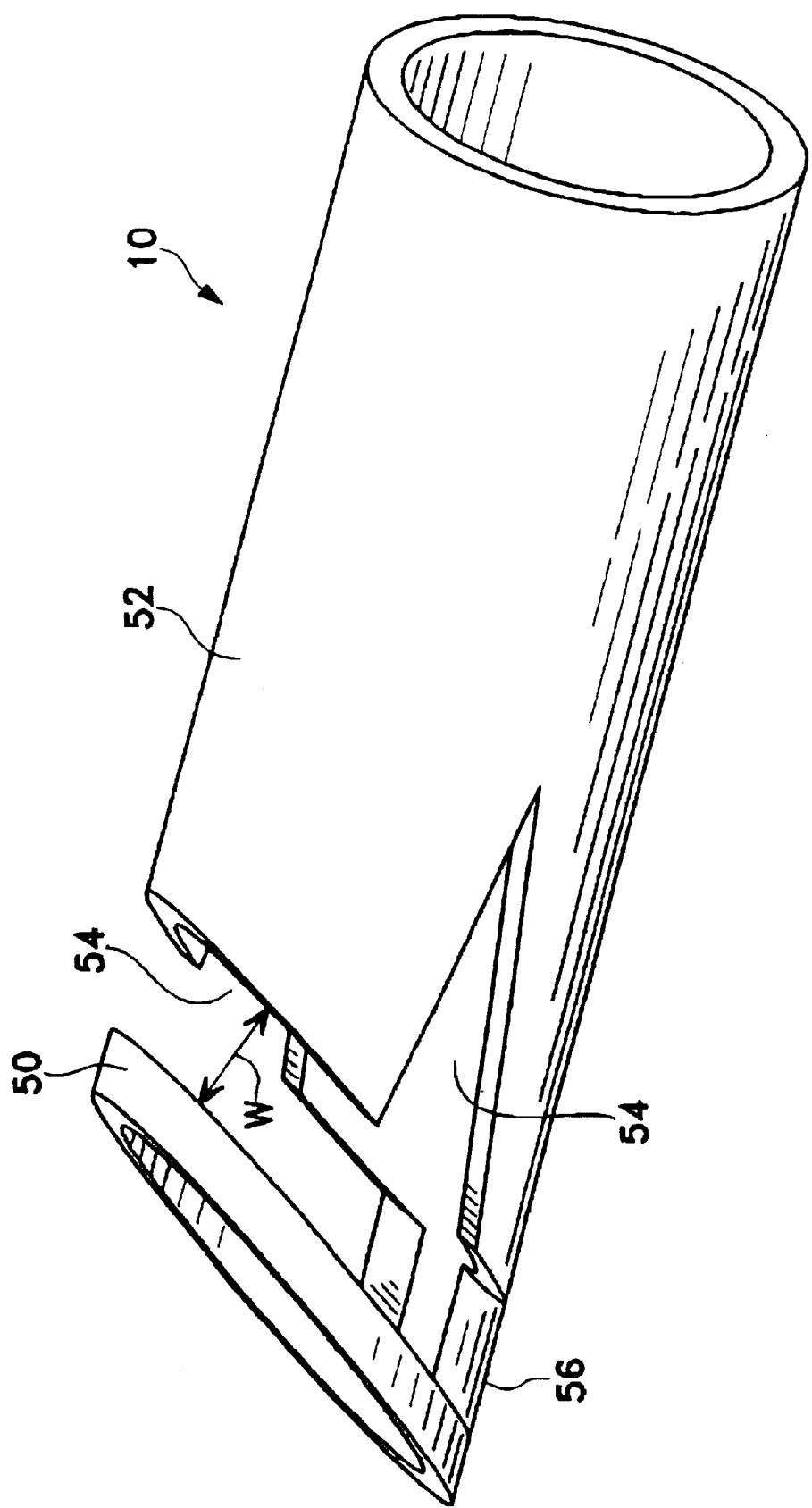
FIG. 7A shows a compressible loading sheath embodiment of the present invention in perspective views.

FIG. 7A shows a compressible loading sheath 10 capable of compressing the end-side fitting upon exposure to an external force. The compressible loading sheath contains a distal tube 52 and a proximal ring 50. The distal tube 52 contains at least one slot 54 on either side of the loading sheath; the illustrated embodiment contains two slots 54. The proximal ring 50 is separated from the distal tube 52 by a distance W. This distance is chosen so that the operator can see that the bypass graft has been appropriately advanced over the base of the end-side fitting. Proximal ring 50 is attached to distal tube 52 using link 56. The proximal ring and the distal tube are fabricated with at least one groove, slit, or series of perforations to enable splitting the loading sheath for removal from around the bypass graft.

Figure 7B:
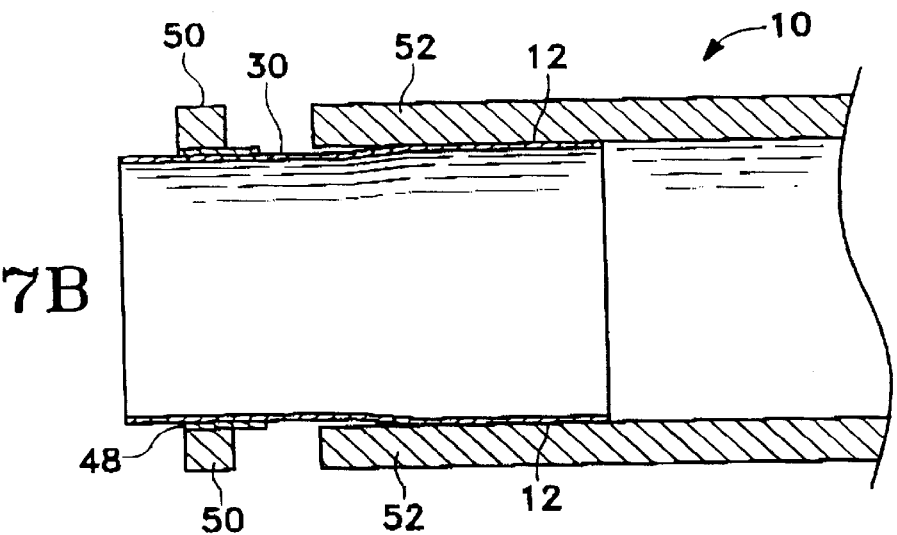
FIGS. 7B to 7C show the steps of positioning a bypass graft over a compressible fitting of the present invention using a compressible loading sheath.
Figure 7C:
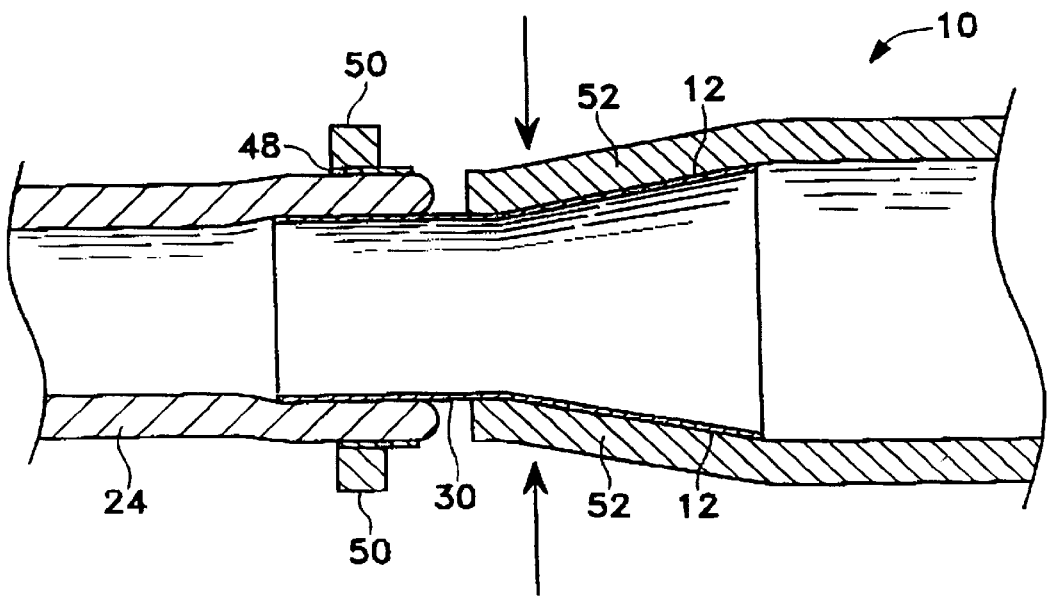

As the sides of loading sheath distal tube 52 bounded by slots 54 are compressed, the base of the end-side fitting is compressed into a reduced diameter, as shown in FIG. 7C. A tool 58 such as that shown in FIG. 7D may be used to exert force on loading sheath 10 causing distal tube 52 and the base of the fitting to compress into a reduced diameter. The tool includes opening 62 into which distal tube 52 of loading sheath 10 is advanced. Handles 60 of the tool are squeezed, decreasing the diameter of the opening and compressing distal tube 52. With base 30 of the fitting in a reduced diameter, bypass graft 24 is readily advanced over the outer surface of the fitting base, as shown in FIG. 7C. As shown in FIGS. 7B and 7C, proximal ring 50 supports retaining ring 48. Once the bypass graft is positioned over the base of the fitting and under retaining ring 48, the external force causing loading sheath 10 to compress is removed, allowing base 30 to expand towards its resting configuration. Bypass graft 24 becomes compressed between fitting base 30 and retaining ring 48, producing a secure bond. As discussed previously, retaining ring 48 may match the base of the fitting to better lock retaining ring to the base. To enhance the ability to position bypass graft 24, link 56 may be fabricated from a relatively flexible material so as to cause ring 48 to be deflected a short distance as the sides of the distal tube are compressed. This produces an opening between base 30 of the end-side fitting and link 56 to better advance bypass graft 24.

As an alternative to retaining ring 48 above, compressible, expandable retaining rings may be used. These expandable retaining rings have a resting inner diameter that is less than the resting outer diameter of the fitting base to ensure the bypass graft is compressed between the retaining ring and the fitting base. This retaining ring may be expanded and supported by proximal ring 50 of loading sheath 10. Once the bypass graft is positioned, the retaining ring is advanced into the gap between proximal ring 50 and distal tube 52. Then, retaining ring 48 returns towards its resting configuration, thereby compressing the bypass graft against fitting base 30. The spring characteristics of the retaining ring and the fitting base are tailored to produce the optimal amount of compression of the bypass graft maintaining the inherent inner diameter of the bypass graft.

The loading sheath may also be used to store the end-side fitting and provide a stabilizer to position and secure the bypass graft. A cap may be placed over the distal end of loading sheath 10 to restrict axial motion of the fitting while positioning and securing the bypass graft. Alternatively, the loading sheath may further function as the delivery sheath.

Figure 8C:
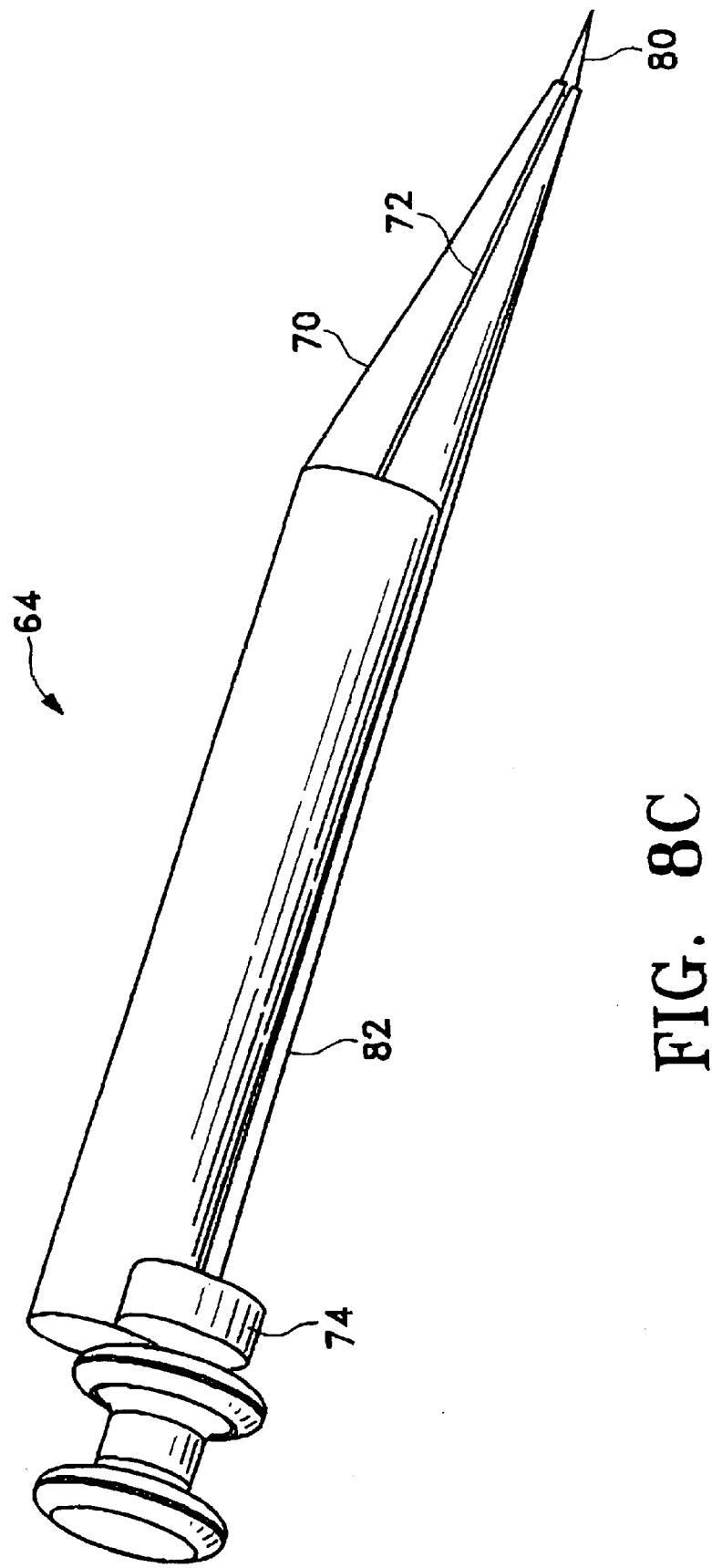
FIG. 8C shows a single motion delivery system of the present invention having a separate lumen to house a perforating mechanism or guidewire.

FIGS. 8A and 8B show an adaptation of a delivery system that combines the tear-away sheath, the dilating member, and plunger into one device. This single motion delivery system is an improvement of the dilating sheath described in U.S. patent application Ser. No. 09/329,503. The single motion delivery sheath 64 contains at least one groove, slit, or series of perforations that enables splitting the delivery sheath for removal from around the bypass graft. At least one (and preferably two) groove, slit, or series of perforations is an extension of the grooves, slits, or series of perforations 72 used to separate tapered distal end 70 of the delivery sheath. This tapered distal end 70 is designed to follow a needle or guidewire through a puncture in the vessel wall and expand the puncture to facilitate inserting the main section of delivery sheath 64 into the host vessel. As shown in FIG. 8C, the delivery sheath may include a separate lumen 82 to house perforating mechanism 80 or guidewire (not shown). This eliminates the concern of passing the perforating mechanism or guidewire between the interior surface of the delivery sheath and the outer surface of the bypass graft and fitting combination, which could abrade or otherwise damage the bypass graft.

Delivery sheath 64 has a central lumen (not shown) adapted to pass the bypass graft and fitting combination. An integrated plunger 68 is used to advance the bypass graft and fitting combination past the tapered end of the dilating sheath and into the host vessel. The handle 74 incorporated in delivery sheath 64 provides an anchor to manipulate integrated plunger 68 without having to hold the delivery sheath tubing. This integrated plunger incorporates a slide mechanism 78 to follow a longitudinal slide opening 66 through the delivery sheath tubing. Integrated plunger 68 includes a distal end 76 that contacts the component of the fitting (e.g., the retaining ring for non-everted conditions or end-side fitting for everted conditions) residing outside the bypass graft. This prevents damaging the bypass graft as the bypass graft and fitting are advanced through the delivery sheath. Distal end 76 of plunger 68 also provides a surface to split the tapered distal end 70 of delivery sheath 64 along the at least one (and preferably four) groove, slit, or series of perforations 72. This functionality is especially important when the end-side fitting is compressible and does not have enough radial stiffness to split tapered distal end 70 itself, even if the compressible end-side fitting has enough radial stiffness to maintain patency of the host vessel opening. Plunger 68 may additionally advance the compression ring over the delivery sheath to simultaneously deploy the end-side fitting within the host vessel and position the compression ring over the base of the end-side fitting.

Tapered end 70 of the delivery sheath must prevent collapsing while inserting through and opening the puncture site, and enable expanding or splitting so the bypass graft and fitting combination may be advanced into the host vessel lumen. The tapered end may be fabricated by slitting the end of the delivery sheath tubing into three or more sections such that each section tapers distally, forming the sections such that they create a single tapered distal end (the sections may overlap partially), and covering the tapered distal end with a material having a low durometer and a large percent elongation (e.g., silicone and urethane). The sections are formed such that they exert radial force to prevent collapsing while the dilating sheath is advanced through the puncture site. The covering provides a fluid-tight coating around tapered end 70 that elongates as the sections are spread apart; this enables expanding the diameter of tapered end 70 while the bypass graft and fitting combination are inserted through the tapered end. An alternative fabrication process eliminates the need for the covering and bonds the sections (whether overlapping or not) with an adhesive. The adhesive holds the position of the tapered end sections and produces a fluid-tight interface between the sections but permits separating the sections as plunger 68 advances the bypass graft and fitting combination through the positioned dilating sheath. Another embodiment involves forming the distal end 70 of the delivery sheath tubing into a taper and creating grooves or a series of perforations 72 at the locations at which the tapered distal end needs to split so to deploy the end-side fitting through the tapered distal end of the delivery sheath.

A further adaptation of tapered end 70 takes advantage of materials having high water adsorption rates. Materials such as cellulose acetate are stiff when dehydrated and extremely flexible when hydrated. The delivery sheath tubing may be fabricated from cellulosics or similar material such that the tapered end is split into three or more sections and formed into a taper. The delivery sheath is allowed to dry where it is relatively stiff and exhibits sufficient column strength to expand the puncture site. Once inside the vessel lumen, the tubing material is exposed to fluid causing it to become more flexible. At this point, the tapered end may be separated into the three or more sections as the bypass graft and fitting combination are advanced into the host vessel.

Application to Robotic Surgery and Less Invasive Surgery

The fitting and delivery system embodiments discussed in this invention are directly amenable to robotic surgery and less invasive (i.e. minimally invasive) surgery involving a thoracostomy to access the anastomosis site. In particular, the fittings and delivery system embodiments of the present invention enable automating the attachment of the bypass graft to the fitting, especially when considering the use of the loading sheath described above. In addition, the use of the delivery system for deploying the fittings and bypass graft is significantly easier to automate than conventional suturing. Finally, the ability to advance the bypass graft and fitting combination along an axis defined by the delivery sheath facilitates automating the deployment of the bypass graft and fitting combination through the delivery sheath and into the host vessel.

For example, robotic arm end effectors of a robotic instrument, such as those described in U.S. Pat. Nos. 5,657,429 and 5,762,458, may be used to manipulate the delivery system to puncture the host vessel wall and insert the delivery sheath into the interior of the host vessel. To accomplish this, the robotic arm end effector positions the perforating mechanism to the desired anastomosis site. An endoscope is used to view the location of the perforating mechanism and direct the positioning of the robotic arm effectors. Once the host vessel is perforated, the dilating mechanism is advanced to expand the opening into the host vessel and the sheath is advanced to produce a conduit into the host vessel interior. A guidewire may be used between the steps of dilating the opening and advancing the sheath so the perforating mechanism may be removed to prevent abrading or perforating the opposite side of the host vessel. This process may be automated by incorporating end effectors that move axially relative to each other to advance or retract the components of the delivery system.

The bypass graft is advanced into the loading sheath, described above, and secured to the fitting. Again, this motion is amenable to automation since the bypass graft is advanced into the loading sheath, which is compressed upon exposure to an external force, and the retaining ring is positioned over the bypass graft to base of the end-side fitting interface.

After securing the bypass graft to the fitting, the fitting and bypass graft combination is inserted through the delivery system using another robotic arm end effector. This may be automated since the operation includes advancing the loading sheath into the delivery sheath along the delivery sheath axis and further advancing the bypass graft and fitting combination through the delivery sheath and into the host vessel along the same delivery sheath axis. Once positioned, the delivery sheath is retracted, split into two pieces, and removed from around the bypass graft. A compression ring is advanced over the base of the fitting, using the same end effector used to advance the bypass graft and fitting combination, to compress the host vessel wall against the fitting petals. In fact, the compression ring may be housed around the loading sheath and advanced over the delivery sheath as the bypass graft and fitting are advanced into the host vessel. This facilitates positioning the compression ring without requiring a separate step and enhances the short-term bond between the host vessel wall and end-side fitting.

The application to robotic surgery is further enhanced with the design of the single motion delivery system. The bypass graft is secured to the base of the end-side fitting, contained in a compressible loading sheath, as described above. Alternatively, the bypass graft may be secured to the base of the end-side fitting, already contained within the single motion delivery sheath, by modifying the design of the delivery sheath to incorporate features of the compressible loading sheath.

After securing the bypass graft to the base of the end-side fitting and loading the fitting and bypass graft combination into the delivery sheath, the delivery system is positioned using the robotic arms at the desired anastomosis site. The perforating mechanism is used to access the interior of the host vessel and the single motion delivery system is advanced through the puncture, thereby dilating an opening through the vessel wall.

Once inside the host vessel, the integrated plunger is used to advance the bypass graft and fitting combination through the single motion delivery sheath and simultaneously open the tapered, split end of the single motion delivery sheath. This eliminates the external force constraining the petals into a reduced diameter.

Once the petals expand towards their resting configuration, the delivery sheath is retracted, also pulling the petals of the end-side fitting into contact with the interior of the host vessel wall.

At this point, the delivery sheath is further retracted, split into two pieces, and removed from around the bypass graft.

As discussed above, positioning the compression ring may be performed while positioning the bypass graft and fitting combination or as a separate step. As this entire deployment and securing process is conducted along an axis defined by the delivery system, this procedure is amenable to robotic surgery and minimally invasive surgery.

When modifying the sutureless anastomosis system for minimally invasive surgery applications, remote operation of the delivery system must be available. This means a long side arm extension must be attached to each component of the delivery system. Exemplary side arm extensions are disclosed in U.S. patent application Ser. No. 09/329,504 and U.S. Provisional Patent Application Serial No. 60/111,948. The side arm extensions function like the robotic arms of robotic instruments in that they provide remote manipulation of the delivery system but do not increase the functional length of the components of the delivery system. The functional length of the delivery sheath (defined as the length between the distal tip and the proximal hub of the delivery sheath) must be long enough to fit past the host vessel wall but should be minimized because the bypass graft must fit through the delivery sheath with enough slack in the bypass graft for the delivery sheath to be retracted, split, and removed from around the bypass graft. The use of the delivery systems of this invention, especially the single motion delivery system, facilitate positioning of the delivery system at the desired anastomosis site and advancing the bypass graft and fitting combination through the host vessel wall.

We claim as our invention:

1. A split wall anastomotic connector comprising:
    a fitting having a base and two opposing sides,
    the fitting being thermally formed so that (1) the two opposing sides are spaced apart from one another when the fitting is in a relaxed, undeployed configuration and (2) the fitting is capable of assuming a generally tubular, deployed configuration in which the two opposing sides are closer to one another than when the fitting is in the relaxed, undeployed configuration,
    the fitting further comprising at least one petal extending from the base, the petal configured to radially expand from the base when the fitting is in the deployed configuration.

2. The connector of claim 1 wherein the petal defines at least one aperture within the petal.

3. The connector of claim 1 wherein the petal comprises a memory elastic material.

4. The connector of claim 1 further comprising a plurality of petals extending from the base along a line that forms an angle of between thirty and ninety degrees with a longitudinal fitting axis that is generally parallel to the two opposing sides.

5. The connector of claim 1 further comprising a compression ring configured to secure the fitting to a vessel when the fitting is in the deployed configuration.

6. The connector of claim 5 wherein the fitting comprises at least one tab configured to self-expand when the fitting is in the deployed configuration to protrude radially from the base and to secure the compression ring to the fitting.

7. The connector of claim 1 further comprising a loading sheath defining a central lumen adapted to receive and compress the fitting into the deployed configuration.

* * * * *